(12) United States Patent
Wu et al.

(10) Patent No.: US 10,276,358 B2
(45) Date of Patent: Apr. 30, 2019

(54) CHEMICALLY MODIFIED ION MOBILITY SEPARATION APPARATUS AND METHOD

(71) Applicants: Ching Wu, Boxborough, MA (US); Mark A Osgood, Brookline, NH (US)

(72) Inventors: Ching Wu, Boxborough, MA (US); Mark A Osgood, Brookline, NH (US)

(73) Assignee: Excellims Corporation, Acton, MA (US)

( * ) Notice: Subject to any disclaimer, the term of this patent is extended or adjusted under 35 U.S.C. 154(b) by 0 days.

(21) Appl. No.: 15/665,421

(22) Filed: Jul. 31, 2017

(65) Prior Publication Data

US 2017/0365454 A1    Dec. 21, 2017

Related U.S. Application Data

(60) Continuation-in-part of application No. 14/537,863, filed on Nov. 10, 2014, now Pat. No. 9,719,963, and a continuation-in-part of application No. 14/992,053, filed on Jan. 11, 2016, now Pat. No. 9,734,998, which is a continuation of application No. 14/214,558, filed on Mar. 14, 2014, now Pat. No. 9,236,234, said application No. 14/537,863 is a continuation of application No. 13/475,993, filed on May 20, 2012, now Pat. No. 8,884,221, and a continuation-in-part of application No. 13/360,758, filed on Jan. 29, 2012, now Pat. No. 8,492,712, which is a division of application No. 12/471,101, filed on May 22, 2009, now Pat. No. 8,106,352, which is a continuation of application No. 11/618,430, filed on Dec. 29, 2006, now Pat. No. 7,576,321, said application No. 13/475,993 is a continuation-in-part of application No. 13/360,760, filed on Jan. 29, 2012, now Pat. No. 8,492,708, and a continuation-in-part of application No. 12/695,111, filed on Jan. 27, 2010, now Pat. No.

(Continued)

(51) Int. Cl.
| | |
|---|---|
| *H01J 49/06* | (2006.01) |
| *G01N 27/62* | (2006.01) |
| *H01J 49/00* | (2006.01) |
| *C07B 63/00* | (2006.01) |

(52) U.S. Cl.
CPC ............ *H01J 49/061* (2013.01); *C07B 63/00* (2013.01); *G01N 27/622* (2013.01); *H01J 49/0027* (2013.01)

(58) Field of Classification Search
CPC .. G01N 27/622; G01N 27/624; G01N 27/626; G01N 21/658; G01N 1/24; H01J 49/0027; H01J 49/061; H01J 49/0036; H01J 49/0445; H01J 49/10; H01J 49/165; H01J 49/167; H01J 49/22
USPC ... 250/282, 288, 286, 287, 281, 283, 396 R, 250/423 P
See application file for complete search history.

(56) References Cited

U.S. PATENT DOCUMENTS

| | | | | |
|---|---|---|---|---|
| 3,845,301 A | * | 10/1974 | Wernlund | G01N 27/622 250/286 |
| 4,777,363 A | * | 10/1988 | Eiceman | G01N 27/622 250/286 |

(Continued)

*Primary Examiner* — David A Vanore

(57) ABSTRACT

An ion mobility spectrometry apparatus and method wherein ions are selected using an AC gate, then separated along a drift axis while providing a drift gas flow in a direction that is substantially neither in the direction of the drift axis nor opposite to the drift axis.

19 Claims, 18 Drawing Sheets

Related U.S. Application Data 8,242,442, and a continuation-in-part of application No. 12/577,062, filed on Oct. 9, 2009, now Pat. No. 8,217,338, said application No. 13/475,993 is a continuation-in-part of application No. 11/776,392, filed on Jul. 11, 2007, now abandoned.

(60) Provisional application No. 61/488,438, filed on May 20, 2011, provisional application No. 60/766,226, filed on Jan. 2, 2006, provisional application No. 61/104,319, filed on Oct. 10, 2008, provisional application No. 60/891,532, filed on Feb. 26, 2007, provisional application No. 60/807,031, filed on Jul. 11, 2006.

(56) References Cited

U.S. PATENT DOCUMENTS

| | | | |
|---|---|---|---|
| 6,509,562 B1* | 1/2003 | Yang | G01N 27/622 250/287 |
| 7,417,222 B1* | 8/2008 | Pfeifer | H01J 49/0027 250/282 |
| 2003/0132379 A1* | 7/2003 | Li | G01N 27/622 250/286 |
| 2008/0073503 A1* | 3/2008 | Wu | G01N 27/622 250/283 |
| 2008/0173809 A1* | 7/2008 | Wu | C07B 63/00 250/283 |
| 2009/0032701 A1* | 2/2009 | Rodier | G01N 27/622 250/282 |
| 2009/0166521 A1* | 7/2009 | McGann | G01N 27/622 250/281 |
| 2009/0212207 A1* | 8/2009 | Griffin | G01N 27/624 250/282 |
| 2009/0238723 A1* | 9/2009 | Guharay | G01N 21/658 422/68.1 |
| 2010/0200745 A1* | 8/2010 | Osgood | G01N 27/622 250/282 |
| 2012/0228491 A1* | 9/2012 | Wu | G01N 27/622 250/282 |
| 2012/0273669 A1* | 11/2012 | Ivashin | H01J 49/0036 250/282 |
| 2014/0346346 A1* | 11/2014 | Wu | C07B 63/00 250/287 |
| 2015/0340221 A1* | 11/2015 | Benner | H01J 49/22 250/282 |
| 2017/0365454 A1* | 12/2017 | Wu | H01J 49/0027 |

\* cited by examiner

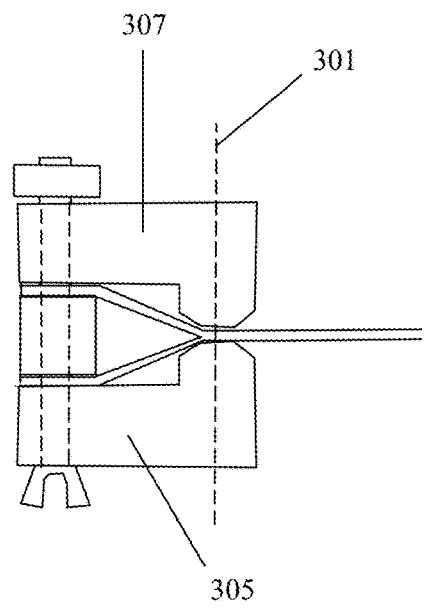 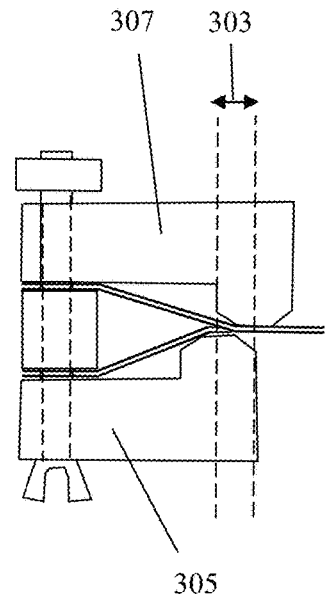
Fig. 3A　　　　　　　　　Fig. 3B
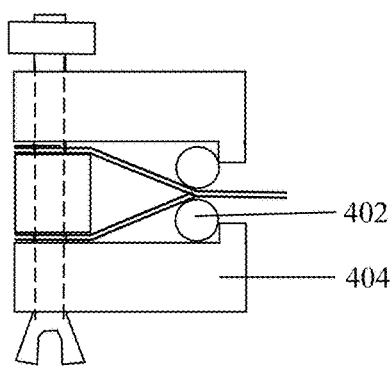
Fig. 4

CHEMICALLY MODIFIED ION MOBILITY SEPARATION APPARATUS AND METHOD

CROSS-REFERENCE TO RELATED APPLICATIONS

The present application is a continuation-in-part of U.S. patent application Ser. No. 14/992,053, filed on Jan. 11, 2016, which is a continuation of application Ser. No. 14/214,558, filed on Mar. 14, 2014, which claims the benefit of and priority to corresponding U.S. Provisional Patent Application Ser. No. 61/784,324, filed on Mar. 14, 2013 and 61/801,722, filed on Mar. 15, 2013, and which is a continuation-in-part of U.S. patent application Ser. No. 12/763,092, filed on Apr. 19, 2010 and now issued as U.S. Pat. No. 9,177,770; the entire content of these applications are herein incorporated by reference.

The present application is also a continuation-in-part of U.S. patent application Ser. No. 14/537,863, filed on Nov. 10, 2014, which is a continuation of U.S. patent application Ser. No. 13/475,993, filed May 20, 2012. Application Ser. No. 13/475,993 is a continuation-in-part of U.S. patent application Ser. No. 13/360,758, filed Jan. 29, 2012 and now issued as U.S. Pat. No. 8,492,712, which is a division of application Ser. No. 12/471,101, filed May 22, 2009, the latter now issued as U.S. Pat. No. 8,106,352, which is a continuation of U.S. patent application Ser. No. 11/618,430, filed Dec. 29, 2006, the latter now issued as U.S. Pat. No. 7,576,321, which claims priority from Provisional Application 60/766,226, filed Jan. 2, 2006. Application Ser. No. 13/475,993 is a continuation-in-part of U.S. patent application Ser. No. 13/360,760, filed Jan. 29, 2012, which is a division of application Ser. No. 12/471,101, filed May 22, 2009, the latter now issued as U.S. Pat. No. 8,106,352, which is a continuation of U.S. patent application Ser. No. 11/618,430, filed Dec. 29, 2006, the latter now issued as U.S. Pat. No. 7,576,321, which claims priority from Provisional Application 60/766,226, filed Jan. 2, 2006. Application Ser. No. 13/475,993 is a continuation-in-part of U.S. patent application Ser. No. 12/695,111, filed Jan. 27, 2010. Application Ser. No. 13/475,993 is a continuation-in-part of U.S. patent application Ser. No. 12/577,062, filed Oct. 9, 2009, which claims priority from Provisional Application 61/104,319, filed Oct. 10, 2008. Application Ser. No. 13/475,993 is a continuation-in-part of U.S. patent application Ser. No. 11/776,392, filed Jul. 11, 2007, which claims priority from Provisional Application 60/891,532, filed Feb. 26, 2007 and claims priority from Provisional Application 60/807,031, filed Jul. 11, 2006. Application Ser. No. 13/475,993 also claims the benefit of and priority to corresponding U.S. Provisional Patent Application No. 61/488,438, filed May 20, 2011. The entire contents of all of the above applications are incorporated herein by reference in their entirety.

BACKGROUND OF THE INVENTION

Many analytical instruments, such as ion mobility spectrometers (IMS), can require a gating device for turning on and off a flowing stream of ions and/or other charged particles. IMS are widely used in field chemical analysis. IMS separate ionic species based on their ion mobility in a given media (either gas or liquid). Recent development of the IMS technology results in two forms of IMS instruments and systems. The time-of-flight (TOF) IMS separate ions based on their steady state ion mobilities under constant electric field. High resolving power with IMS has been achieved with the TOF-IMS instruments. Alternatively, devices that separate ions based their mobility changes under high field conditions, such as field asymmetric ion mobility spectrometer (FAIMS) or differential mobility spectrometer (DMS), can also be used.

Even though the gating device is a minor component in the overall design of an IMS, if manufactured correctly, this component can improve the IMS resolution and system performance. The gating device is used to regulate the injection of ion packets into the analytical instrument. There are many deficiencies with the current approaches for manufacturing gating devices.

Traditionally the gating device has been used to regulate the injection of ion packets into the analytical instrument. Even though the gating device is a minor component in the overall design of an IMS, this device is an important part that can improve the level resolution between peaks in the IMS by providing a compact ion packet without significant diffusion. Many inventions have been proposed around the manufacturing and designing the gating device for improving the resolution without major improvements. The present invention modifies the gating device in a manner that improves peak resolution and is able to control which size ions are injected into the analytical instrument. This novel gating device significantly reduces the analysis of complex samples with multiple components such that lower mobility ions are not able to enter the drift tube.

Since it was invented in the early 1970's, ion mobility spectrometry (IMS) has been developed into a powerful analytical tool used in a variety of applications. There are three major forms of this instrument including independent chemical detection systems, chromatographic detectors, or hyphenated IMS mass spectrometry (MS) systems. As an independent detection system, IMS qualitatively and quantitatively detects substances in different forms relying on its capability to ionize the target substance, to separate the target substance from background based on interactions with a drift gas (i.e. a carrier gas), and to detect the substance in its ionized form. As a chromatographic detector, IMS acquires multiple ion mobility spectra of chromatographically separated substances. In combined IMS-MS systems, IMS is used as a separation method to isolate target substances before mass analysis. However, the resolution of IMS is generally consider low, often regulating such devices to qualitative use or use in environments with low levels of interferants with respect to the substances of interest.

The basic common components of an IMS system consist of an ionization source, a drift tube that includes a reaction region, an ion shutter grid, a drift region, and an ion detector. In gas phase analysis the sample to be analyzed is introduced into the reaction region by an inert carrier gas, ionization of the sample is often completed by passing the sample through a reaction region and/or a radioactive 63Ni source. The ions that are formed are directed toward the drift region by an electric field applied to drift rings that establish the drift region, and a narrow pulse of ions is then injected into, and/or allowed to enter, the drift region via an ion shutter grid. Once in the drift region, ions of the sample are separated based upon their ion mobilities and their arrival time at a detector is an indication of ion mobility which can be related to ion mass. However, it is to be understood that ion mobility is not only related to ion mass, but rather is fundamentally related to the ion-drift gas interaction potential which is not solely dependent on ion mass.

Ion mobility spectrometers (IMS) have become a common tool for detecting trace amounts of chemical and/or biological molecules. Compared to other spectrometric chemical analysis technologies, e.g., mass spectrometry, IMS is a relatively low resolution technique. The IMS advantages of very high sensitivity, small size, low power consumption, and ambient pressure operation are in some cases completely offset, or at a minimum, reduced by the lack of sufficient resolution to prevent unwanted responses to interfering chemical and/or biological molecules. The false positives that result can range from minor nuisances in some scenarios to major headaches in others. Interfering chemical and/or biological molecules can have very similar ion mobilities which in turn can significantly limit detecting and identifying low levels of the targeted chemical and/or biological molecules in the sample.

The present state of the art ion mobility spectrometers lack the ability to directly reduce the occurrence of interfering chemical and/or biological molecules in a sample's analysis. It is the purpose of this invention to overcome these obstacles by making the use of a cross-directional gas flow in a drift tube and/or using a segmented drift tube for pre-separation.

SUMMARY OF THE INVENTION

The present invention generally relates to systems and methods for transmitting beams of charged particles, and in particular to such systems and methods that employ deflecting at least one set of grid elements into the same plane, such that the grid elements are interleaved.

In one embodiment of the present invention, at least one electrically substrate (conducting or non-conducting) is used to deflect at least one set of the grid elements into the same plane, such that the grid elements are interleaved. The ion gate has a first and second set of electrically isolated grid elements that lie in the same plane where the respective sets of grid elements are applied to alternate potentials. The advanced grid manufacturing methods and features are disclosed.

The present invention generally relates to systems and methods for transmitting beams of charged particles, and in particular to such systems and methods that let only a portion of ions to the drift tube of the IMS by employing an AC voltage (generated by one or more AC power supplies) on the gate wires. By using an AC voltage there is a reduction in the size of the ion depletion area in front of the gate when it is closed, thereby providing a higher peak resolution. In addition the AC gate can be used to separate ions.

The present invention relates to a cross-directional drift tube design for an ion mobility spectrometer wherein the drift gas flow is in a direction that is substantially neither parallel nor antiparallel to the drift axis of ions. A cross-directional drift tube with one or more drift segments allows rapid drift tube clean up and flexible drift media control. A segmented drift tube is used for pre-separation of complex sample before separating samples in the subsequent drift segments. The cross flow design and segmented drift tube can also be used together for enhanced separation performance. In another aspect of the present invention, at least one chemical modifier is added to the drift gas in a cross-directional gas flow that interacts selectively with at least one component of the sample in a drift tube. The component may be impurities and/or interferences in the sample whereby the chemical modifier enhances sample resolution by shifting the components drift times. The chemical modifier interaction forces may include hydrogen bonding, dipole-dipole, and steric hindering effects, but are not limited to only these.

The present invention also relates to various aspects of Multi-Dimensional Ion Mobility Spectrometry (MDIMS) methods and apparatus. In various embodiments, the MDIMS of the present inventions differentiate themselves from conventional ion mobility spectrometry (IMS) by innovatively integrating multiple ion mobility based separation steps in one device. In various embodiments, the present invention provides higher resolution and higher sensitivity than conventional IMS devices and operational approaches. Various embodiments of the present invention provide an integrated multiple dimensional time-of-flight ion mobility spectrometric system that ionizes, separates, and detects chemical species based on their ion mobilities. These systems generally include: (a) at least one ionization source, (b) at least two drift regions, and (c) at least one ion detection device. In various embodiments, these systems separate ions in one drift dimension under one set of drift conditions; and subsequently, the separated ions are introduced into a higher dimension for further separation under the same or a different set of drift conditions. In various embodiments, the separation process can be repeated for one or more additional drift dimensions. Also, in various embodiments, the first drift dimension is used as one or more of an ionization source, reaction region or desolvation region, and drift region for the system. For example, in various embodiments, the electric field in the first drift dimension (first drift tube) can be used as a desolvation region for charged droplets.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

FIGS. 3A and 3B show two different methods to deflect the grid elements.

FIG. 4 shows an alternative method to deflect the grid elements.

DETAILED DESCRIPTION OF VARIOUS EMBODIMENTS

Figure 1:
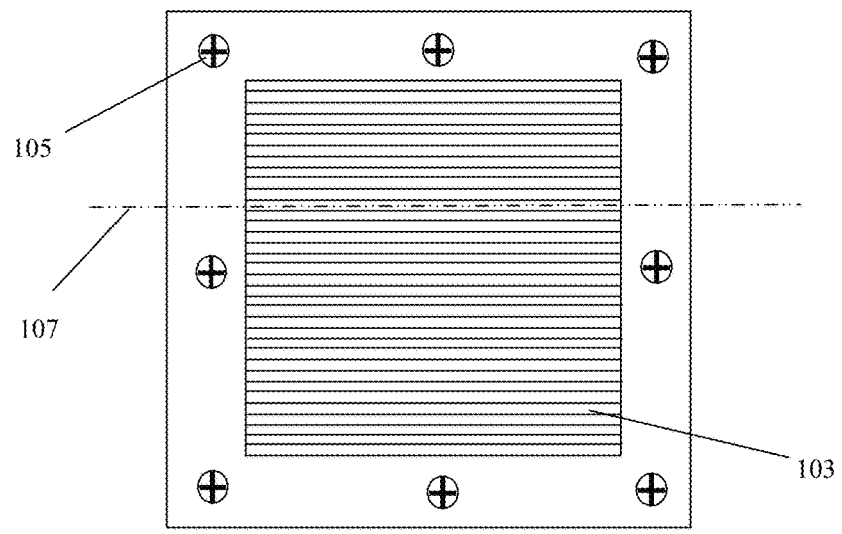
FIG. 1 shows the completed ion gate from a front view.

The terms ion mobility separator, ion mobility spectrometer, and ion mobility based spectrometer are used interchangeably in this invention, often referred to as IMS, including time-of-flight (TOF) IMS, differential mobility spectrometers (DMS), field asymmetric ion mobility spectrometers (FAIMS) and their derived forms. A time of flight ion mobility spectrometer and its derived forms refers to, in its broadest sense, any ion mobility based separation device that characterizes ions based on their time of flight over a defined distance. A FAIMS, a DMS, and their derived forms separate ions based on their ion mobility characteristics under high values of normalized electric field.

The systems and methods of the present inventions may make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc. In many cases, a drift tube also refers to the ion transportation and/or ion filter section of a FAIMS or DMS device.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is, the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, therefore a steady-state ion mobility is achieved.

The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "particle" is intended to mean chemical and/or biological single or plurality of sub-atomic particle, atom, molecule, large or macro molecule, nanoparticle, or other matters that are vapor, droplets, aerosol, liquid, solid that follow a mobile medium, where the medium can be a gas, a liquid, super-critical fluid and/or other fluidic materials.

The present invention generally relates to systems and methods for transmitting beams of charged particles, and in particular to such systems and methods that employ deflecting at least one set of grid elements into the same plane.

As used herein, the term "grid element" generally refers to wire, rod, cable, thin metal foil piece that can be planar, square, rectangular, circular, elliptical, semi-circular, triangular, but not limited to these examples. The grid element can be made of any electrically conducting material.

The term "gate element" generally refers to a structure that includes one or more grid elements that can be spatially arranged with a gap between each other.

The axis of the drift tube along which ions move under the influence of the electrical drift field is referred to herein as a drift axis. The drift axis is often, but not necessarily, a longitudinal axis of the drift tube.

As used herein, the term "analytical instrument" generally refers to ion mobility based spectrometer, MS, and any other instruments that have the same or similar functions. Unless otherwise specified in this document the term "mass spectrometer" or MS is intended to mean any device or instrument that measures the mass to charge ratio of a chemical/biological compounds that have been converted to an ion or stores ions with the intention to determine the mass to charge ratio at a later time. Examples of MS include, but are not limited to: an ion trap mass spectrometer (ITMS), a time of flight mass spectrometer (TOFMS), and MS with one or more quadrupole mass filters.

Figure 6:
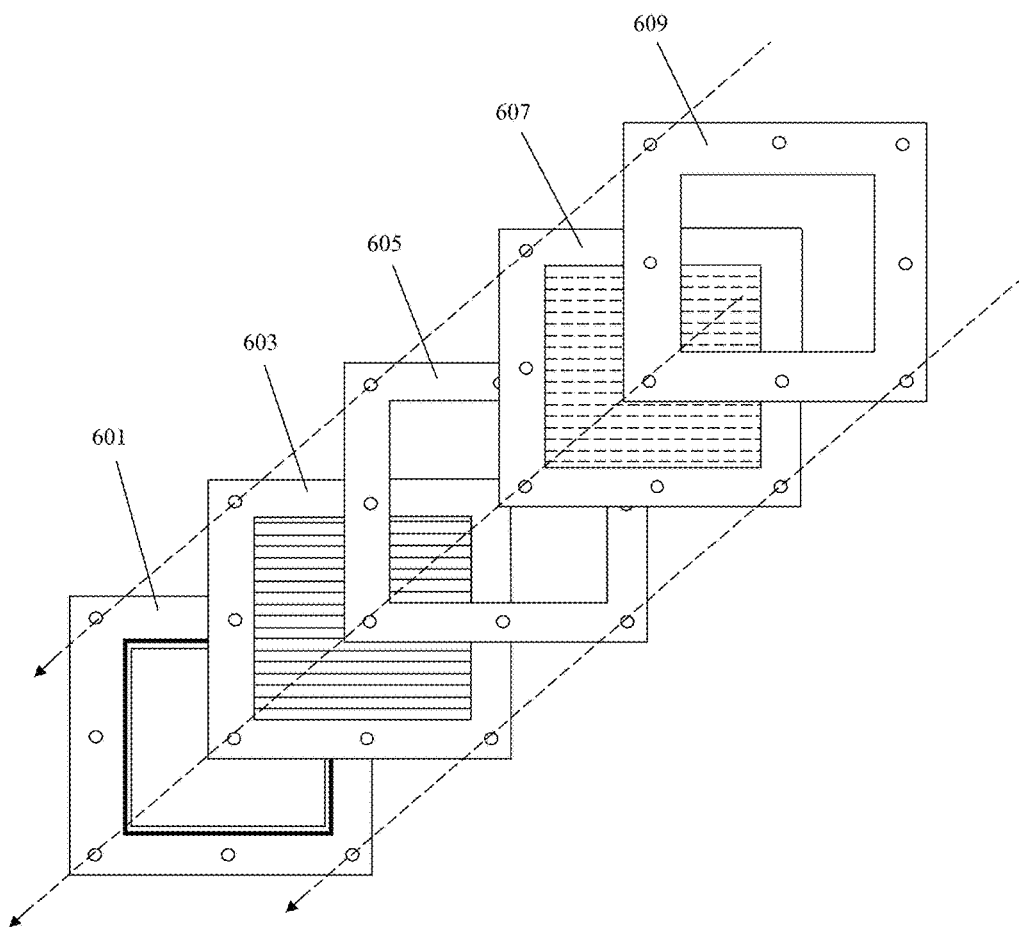
FIG. 6 illustrates the process of manufacturing the ion gate.

One aspect of the invention relates to manufacturing an ion gate in such a way that the ion gate can be produced in a simple, reproducible, and reliable manner. FIG. 6 illustrates a non-limiting process for manufacturing the ion gate. This method for manufacturing an ion gate for a charged particle stream begins with the fabrication of the gate elements 603 and 607 that includes the grid elements. Each of the gate elements 603 and 607 are made so that the two different pairs of grid elements can be interleaved without contacting each other. Followed by assembling an insulating layer (electrically non-conductive, the insulating layer can be any size and shape, such as a square or a disk with openings, or a washer, that allows a different potential to the gate elements) 605 between the gate elements 603 and 607 to electrically isolate the gate elements. The substrate throughout this patent is typically non-conducting, but can also be a conducting material for some applications. Then two electrically non-conductive substrates 601 and 609 are added to deflect the grid elements in the gate elements into the same plane. FIG. 6 shows a non-limiting example, wherein two electrically non-conductive substrates are used. Similarly, one electrically non-conductive substrate can also be used to manufacture the ion gate. Finally, the gate elements are secured together along with the electrically non-conductive substrates and the insulating layer. In an alternative embodiment, the gate elements can be segmented, thus each segment of the grid elements can be operated independently, i.e. open and close at different timing, as a segmented ion gate. The method for manufacturing an ion gate for a charged particle stream, can comprise of electrically isolated grid elements that lie in the same plane. The respective sets of grid elements can be applied to alternate potentials to close the gate and the same potential to open the gate. For example, the grid element is at 100 volts above and 100 volts below the reference potential. The reference potential is the potential at the particular location of the gate in the drift tube. The steps used to manufacture the ion gate can be in any order and comprise: fabricating at least two gate elements, wherein each gate element includes at least one set of grid elements; assembling an insulating layer between the gate elements; deflecting at least one set of grid elements into the same plane of the other set of grid elements with at least one substrate; and securing the gate elements and the non-conductive substrates together.

A non-limiting example of the completed ion gate is shown in FIG. 1. The shape of the ion gate can be: square (shown), oval, circle, semicircle, triangle, rectangle, polygon, octagon, but not limited to these examples. FIG. 1 shows a front view of the completed ion gate. The ion gate includes gate elements that contain the grid elements 103 are held in place with several screws 105. The ion gate apparatus that is used for gating a charged particle stream comprises: at least two sets of grid elements that individual voltages can be applied to each set to open and close; and at least one substrate for deflecting at least one set of grid elements into the same plane of the other sets of grid elements. In addition an electrically insulating layer can be added to allow different voltages to be set to each set of grid elements.

Another aspect of the invention relates to providing an ion gate with an effective gating function by applying a uniform tension on the grid elements, fabricating the gate elements such that the grid elements are equally spaced, and deflecting the grid elements into the same plane.

Figure 2:
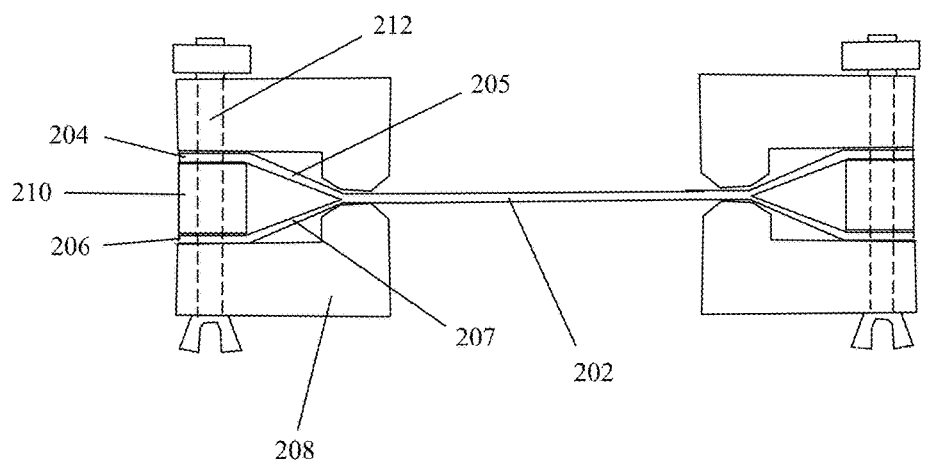
FIG. 2 shows a cross-sectional top view of the ion gate.
Figure 5A:
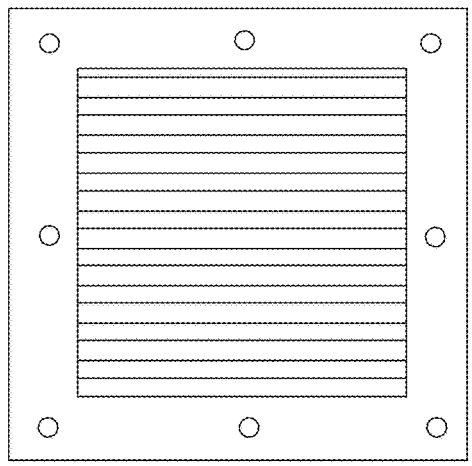
FIGS. 5A-5C illustrates the respective sets of gate elements.
Figure 5B:
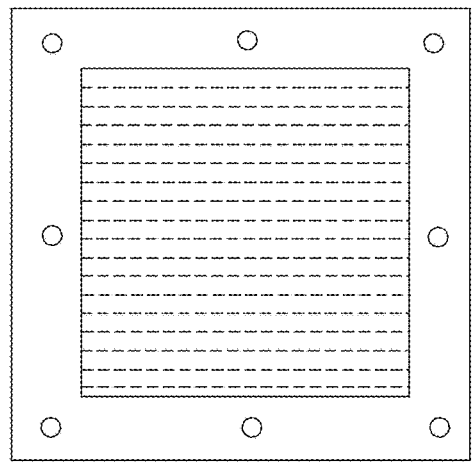
Figure 5C:
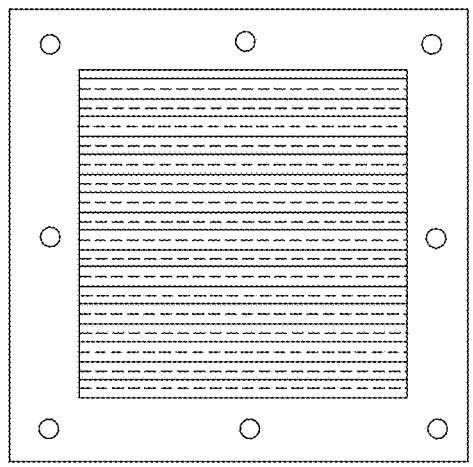

FIG. 2 shows a cross-sectional top view of the ion gate. The cross-section shown in FIG. 2 is indicated in FIG. 1 with a cutting line 107. The ion gate comprises a first and second electrically isolated gate elements 204 and 206 that each have at least one grid element 205 and 207. The electrically non-conductive or conductive substrate 208 deflects the grid element 207 which is part of the gate element 206 into the same plane as the deflected grid element 205 which is part of the gate element 204. The gate elements 204 and 206 are electrically isolated by placing an insulating layer (electrically non-conductive or conductive) 210 between these gate elements. The grid elements are deflected into the same plane 202 and are electrically isolated by interleaving these sets of grid elements with a gap between each grid element. FIG. 5C illustrates the respective sets of grid elements in FIG. 5A and FIG. 5B interleaved. In FIG. 2, the ion gate components are secured together with a screw fastener 212. In this non-limiting example, ether an electrically non-conducive material screw fastener may be used or a conductive material fastener can be contained in an electrically non-conductive standoff (not shown).

One embodiment of the present invention, involves using off-set electrically non-conductive or conductive substrates to deflect the grid elements. FIG. 3A shows the electrically substrates 305 and 307 with no off-set 301. FIG. 3B shows electrically substrates 305 and 307 with an off-set 303. This off-set design may allow uniform deflection of grid elements and low cost manufacturing.

Another embodiment of the present invention, involves the shape of the electrically non-conductive or conductive substrate to deflect the grid elements. The portion that deflects the grid element can be in the shape of a wedge, hexagon, semi-circle, but not limited to these examples. In addition, the electrically non-conductive substrate portion that deflects the grid element can be independent to the secured electrically non-conductive substrate. A non-limiting example is shown in FIG. 4, where a circular (not limited to only this shape) substrate 402 deflects the grid element and the secured substrate 404 holds the substrate 402 in place.

Yet another embodiment of the present invention is the fabrication of the gate elements. The grid elements within the gate elements can be produced by cutting, etching, evaporation or electroplating, but not limited to these methods. In a non-limiting example, parallel rows of grid elements are formed by removing portions of a given thickness of planar metal foil by etching portions from the foil. This method forms a plurality of grid elements that are equally spaced. In addition to forming equally spaced grid elements within the gate element, the grid elements are made from the same gate element material as a single entity. In this manner, the grid elements do not need to be fixed to the gate element through gluing (epoxy), glass soldering, or any other attaching manner. Fabricating the gate elements by etching the grid elements is a robust and reproducible method for manufacturing the grid elements. In addition, since no gluing, soldering, or other attaching manner is used in fabricating the gate elements, elevated temperatures and/or thermal expansion of the grid elements are all uniform. The photo chemical milling (etching) can be performed on one side or both sides of the material being etched.

Figure 7A:
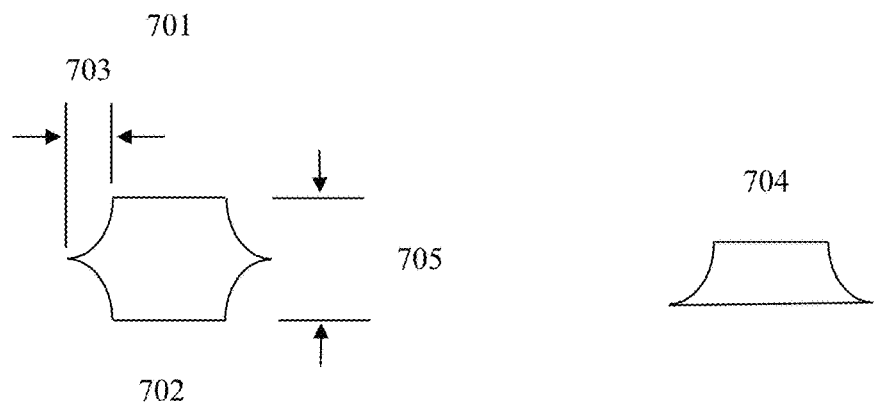
FIG. 7A-7C shows the photo etched edges of the grid elements.
Figure 7B:
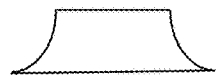
Figure 7C:
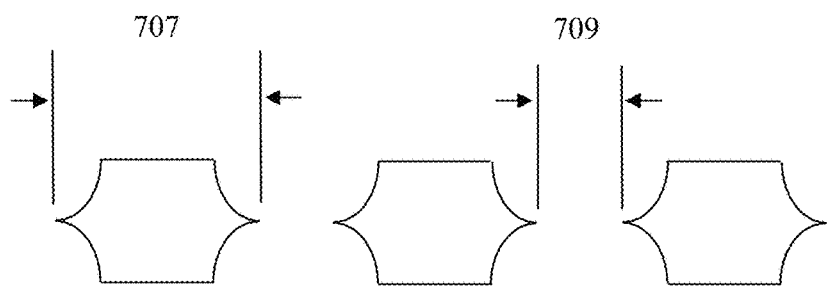

FIG. 7A shows the shape (a pair of opposing concave fillets) of the grid element etched on both sides of the material, etched from the top 701 and the bottom 702 of the material. FIG. 7B shows the shape (a concave fillet) of the grid element etched on one side of the material, etched from only the top side 704 of the material. The etched edge distance 703 may be smaller or greater than the material thickness 705 depending on the layout of the grid elements. For example, the etched edge distance to the material thickness ratio is greater than zero, in particular 1-50%, 50-100%, 100-500%. FIG. 7C shows three grid elements that are etched on both sides of the material. Photo chemical milling can produce uniform dimensions in grid element width 707 and gap 709 between grid elements forming a plurality of grid elements that are equally spaced. When the ion gate is a uniform product, injection of ion packets into the drift tube are tight packets with limited background signal, therefore a higher signal to noise ratio can be achieved. In this embodiment, regardless of manufacturing methods, the grid element is to be made with a sharp edge, the geometry may generate a narrow gating electric field region resulting in high precision gating of charge particles. In an IMS device, a narrow ion pulse could be generated with precision gate timing control. An ion gate apparatus for gating a charged particle stream comprises: at least two sets of electrically insulated grid elements on the same plane, the evenly spaced grid elements have at least one sharp edge face to adjacent grid element.

Another embodiment of the present invention is securing the gate elements together with non-conductive substrates and the insulating layer. The ion gate can be secured by clamping, soldering, screws, pins, but not limited to these examples. The insulating layer can be made from any non-conductive material such as, ceramic, aluminum nitrate, but not limited to these examples.

An alternative embodiment of manufacturing an "Tyndall" type of ion gate for a charged particle stream involves two sets of electrically isolated grid elements, wherein the first set of grid elements is arranged with an offset in respect to the second set of the grid elements, such that the gaps of the first grid element is aligned with the second grid elements; each set of grid elements is applied to alternate potentials when the gate is closed and same potential when the gate is opened. The method involves the steps of: fabricating at least two gate elements by removing portions of a substantially planar metal foil to form a plurality of grid elements; wherein each gate element includes at least one set of grid elements; assembling an insulating layer between the gate elements; and securing the gate elements together.

Figure 8:
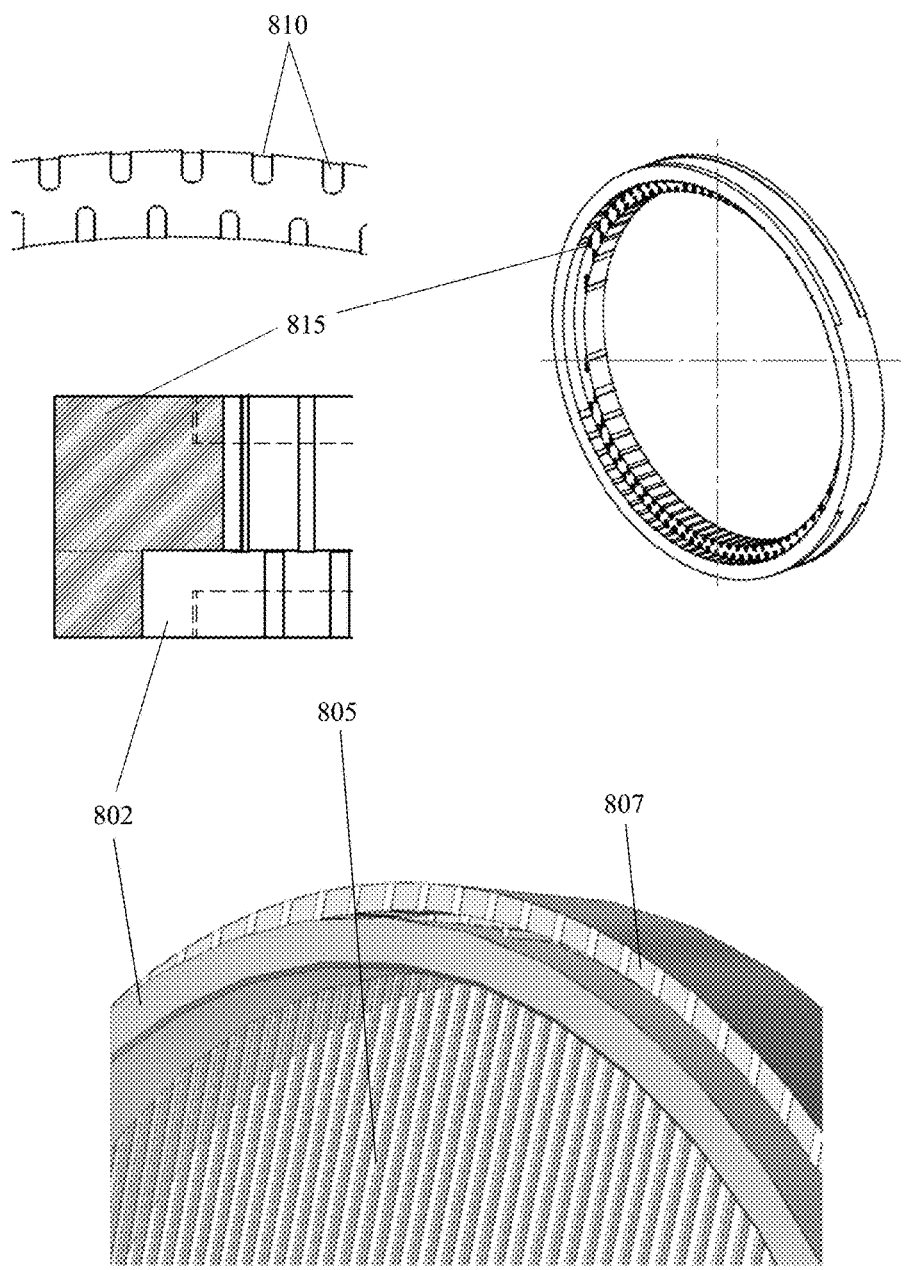
FIG. 8 schematically shows a construction of a Bradbury-Nielsen ion gate using metalized dielectric rings and parallel wires.

In another embodiment of the invention, a metalized dielectric structure is used for the Bradbury-Nielsen gate. A ceramic material is coated with single or multiple layers of metallization materials. The metallization process is commonly finished with a thin layer of nickel, gold or other inert metal for enhanced chemical resistivity. FIG. 8 shows a unique construction method of a Bradbury-Nielsen ion gate using a metalized ceramic material. It is built with a frame ring, a tension ring 802 and parallel wires 805 that are pre-winded on a metal frame. One or the rings, either the frame ring or the tension ring is metalized 815 with a pattern 810 that connects every other wire to each other. In one embodiment, the frame ring has metalized contacts 807 that are 1 mm apart (center to center). During the ion gate construction, the parallel wires are lined up with these contacts and form a firm contact while the tension ring is pushed down into the frame ring. As the wire is selected to match the thermal expansion of the frame ring and tension ring, the wires can be maintained parallel while the IMS is operated under different temperature conditions. The gate control voltage(s) are applied to the wires by attaching an electrical lead to the contact point that is on the outside of the frame ring. Not only for metalized ceramic tube IMS design, the Bradbury-Nielsen ion gate can be used for other analytical instruments.

In various embodiments for symmetric IMS, an ion focusing method can be employed to guide ions to a target collection area on the collector. Suitable focusing methods may include, but are not limited to, static electric field focusing and ion funnel focusing. An ion collector can be segmented to facilitate, collection of ions with specific ion mobility (drift time) or a certain range of mobilities on to different segment of the ion collectors. A segmented Bradbury-Nielson gate can be used to enhance the separation and collection.

Figure 9:
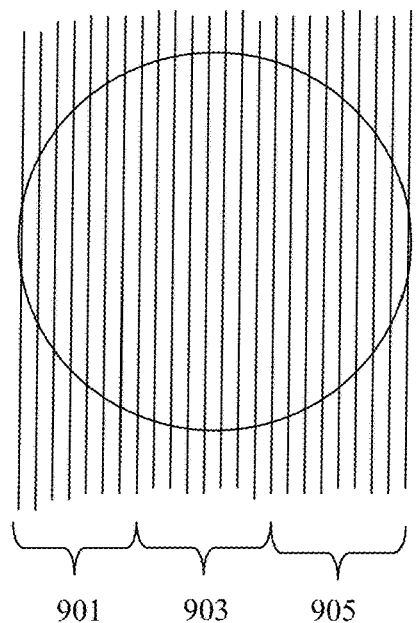
FIG. 9 is a schematic example of a segmented Bradbury-Nielson gate.

In various embodiments of IMS instruments, wherein the Bradbury-Nielsen gate can be segmented. A variety of geometries, including but not limited to parallel, rectangular, concentric ring shape, can be used for the segmentation, referring to FIG. 9, various embodiments can use parallel segmentation. Each segment of the ion gate, for example, 901, 903, and 905, can be controlled to open at a different time. Such a segmented ion gate can be used as either first or second ion gate in a time-of-flight type ion mobility separator. While it is used as the second ion gate in a IMS, multiple portions of ions with different drift time are allowed to pass through segmented ion gate, thus collected on different sections of ion collectors, and recovered separately if desired.

In various embodiments, an apparatus of ion gate for an ion mobility separator comprising a segmented Bradbury-Nielson that contains multiple sections of Bradbury-Nielsen gate. The segmented Bradbury-Nielsen gate can be used as a second gate in a time-of-flight type ion mobility separator. The segmented Bradbury-Nielsen gate comprises a variety of geometries which may include but is not limited to: parallel, rectangular, concentric. The ion mobility separator further comprises a segmented ion collector where a plurality of sections of ion collector is inline with the sections of the segmented Bradbury-Nielson gate.

This invention further describes a method and apparatus of ion gate operation. In one embodiment, an AC voltage is used to close the gate. In a common operation of the Bradbury-Nielsen gate, the ion gate is open when the adjacent grid elements are at the same potential and the ion gate is closed when a DC voltage, e.g. 30V, 50V, 100V, 200V, or −30V, −50V, −100V, −200V are applied on the adjacent grid elements. The voltage creates an electric field that pushes ions toward the grid element that is a lower potential, thus preventing ions from penetrating through the ion gate when closed.

Figure 10:
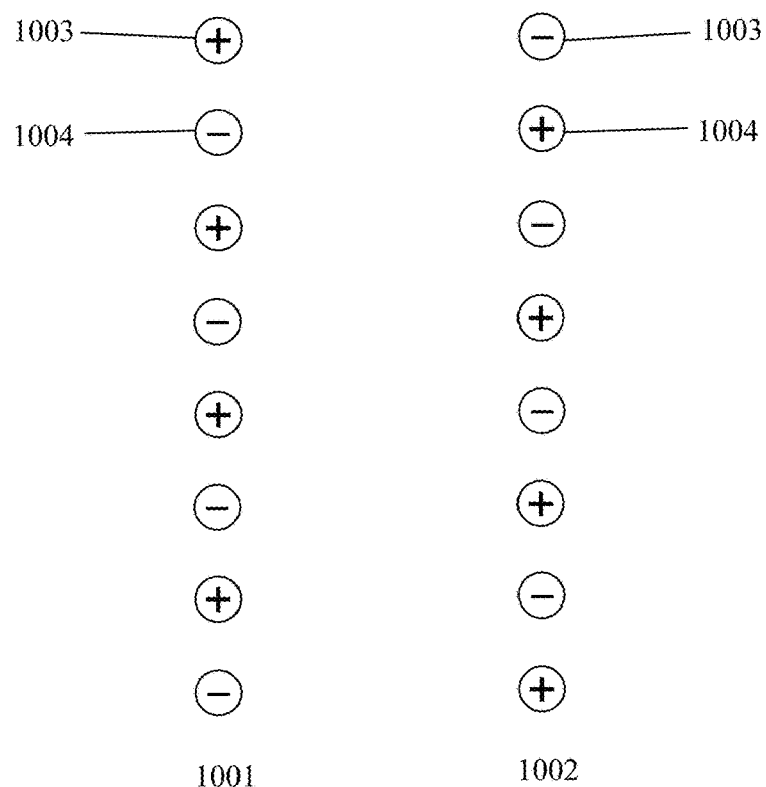
FIG. 10 illustrates an operation method of an ion gate.

During ion mobility measurements, the ion gate is opened for a short period of time, e.g. 100 microseconds, and then closed for a period of time, e.g. 20 millisecond, while ions are traveling in the drift tube. FIG. 10 illustrates a closed ion gate. When the applied voltage is higher than the reference potential, a '+' is shown for the gate wire (i.e. grid element) and when the applied voltage is lower than the reference potential, a '−' is shown for the gate wire. The voltage difference between the adjacent wires causes positive ions to be collected on the (−) wire and negative ions to be collected on the (+) wire. By repeating wire layout pattern of (+) and (−) wires, a large area is covered and ions are prevented to pass through the ion gate. In this embodiment, an AC voltage instead of DC voltage is applied the gate wires. In this case, the potential of each wire is constantly changing. The potential on wire 1003 is '+' and wire 1004 is '−' at the state 1001, and then the potential on wire 1003 is '−' and wire 1004 is '+' at the state 1002. The state 1001 and 1002 repeats at certain frequency. The voltage and frequency of the AC applied to the adjacent wires is optimized to completely close the ion gate. The ion gate is opened by setting all gate wires at the same potential. The new gate configuration and operational method is not limited to be used for ion mobility spectrometer, but can be used for any device that needs to shut off a stream of charged particles.

Figure 21:
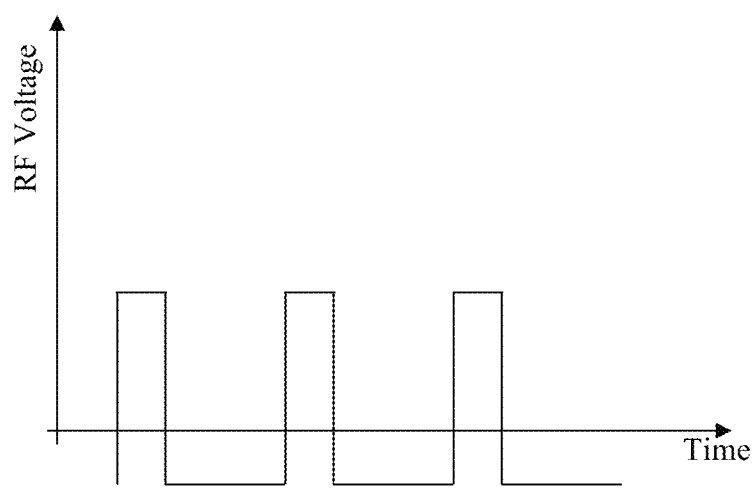
FIG. 21 shows a typical asymmetric waveform used for differential ion mobility spectrometer or field asymmetric ion mobility spectrometer.

In a variety of the embodiments, a method for operating an ion gate for a charged particle stream involves opening the ion gate by setting adjacent gate wires (grid elements) at the same potential; closing the ion gate by setting adjacent gate wires at different potentials by applying an AC voltage to the adjacent wires. The AC voltage can be controlled to provide a given frequency and amplitude that that is most suitable for the intended operation. The frequency can be a constant and/or controlled to cover a broad range during a period when the ion gate is closed. Similarly, the amplitude can be a constant and/or controlled in a range during a period of closing the gate. The AC voltage may be a symmetric or asymmetric waveform (for example, a waveform is used for DMS and/or FAIMS, a typical example of the waveform is shown in FIG. 21). In a variety of operation modes, the AC powered ion gate can be operated as such, conducting a series of ion mobility measurements under a series of different frequencies and/or amplitudes, and then integrating the series of ion mobility measurement data into an ion mobility spectrum using common data processing algorithms, such as summing.

A Bradbury-Nielson gate is traditionally used for injecting short pulses of ions into TOF mass spectrometers and ion mobility spectrometers to improve the mass resolution of TOF instruments by reducing the initial pulse size as compared to other methods of ion injection. Therefore the precise control of the ion pulse width admitted to the drift tube can be controlled. However, the means for controlling the size of ions entering the drift tube using a Bradbury-Nielson gate has not been proposed to date.

Figure 11:
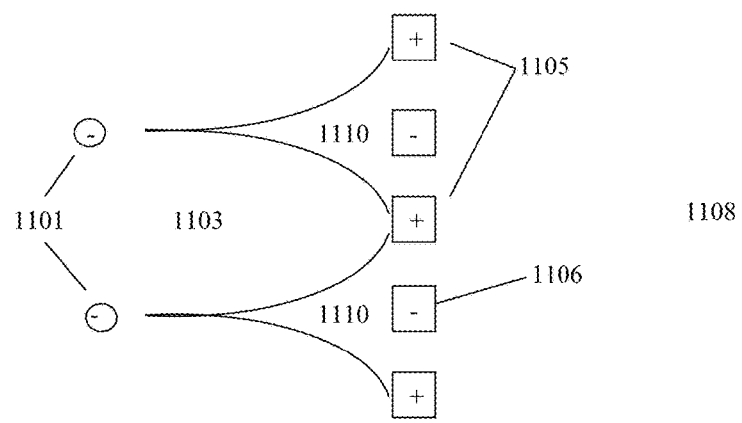
FIG. 11 shows an example of a gate using DC voltage.

One embodiment of the present invention is to use an AC voltage instead of the commonly used DC voltage to control the amount of a ion pulses generated and let through the gate. In a common operation of the Bradbury-Nielson gate, the ion gate is open when the adjacent grid elements are at the same potential and the ion gate is closed when a DC voltage, e.g. 30V, 50V, 100V, 200V, or −30V, −50V, −100V, −200V are applied on the adjacent grid elements. The voltage creates an electric field that pushes ions toward the grid element that is a lower potential, thus preventing ions from penetrating through the ion gate when closed. FIG. 11 shows an example of a gate using DC voltage. Negative sample ions 1101 travel toward the ion gate wires 1105 and 1006 of the gate in a relatively straight line according the applied filed in the reaction region (desolvation region) 1103 until they come close to the gate wires where they are pulled toward the positive wires 1105 and are neutralized on the positive wires 1105 if the gate is not in the open state. Since DC voltage is being used to control the gate, each adjacent wire has a different polarity, either positive or negative. Therefore gate wires 1105 are positive and gate wires 1106 are negative. During ion mobility measurements the ion gate is opened for a short period of time, e.g. 100 microseconds, and then closed for a period of time, e.g. 20 millisecond, thereby letting a pulse of ions travel in the drift tube 1108. During the closed state of the gate an ion depletion area is formed 1110. The larger the area of the ion depletion area the longer the gate needs to be opened to let ions through, since there is a low population of ions. In order to get higher resolution peaks in the IMS spectrum, a shorter opening period of time is preferred in order to get a narrow pulse of ions through with limited diffusion. By using an AC voltage instead of a DC voltage to close the gate the ion depletion area can be reduced, in particular, by a half. The ion depletion area can be reduced by an percentage by using an AC voltage.

Figure 12:
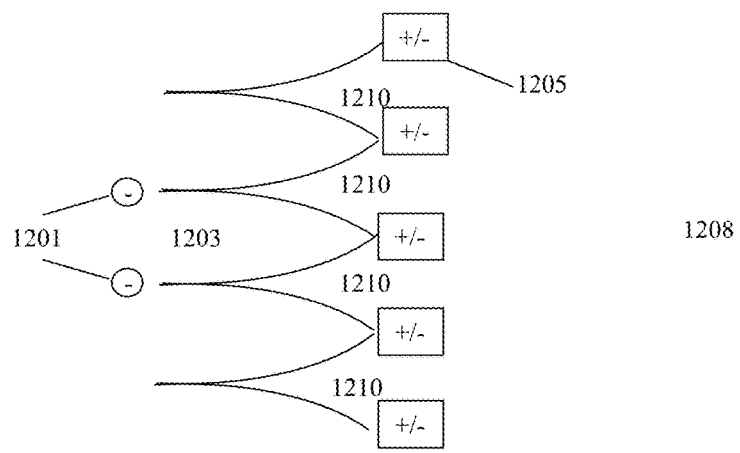
FIG. 12 shows an example of a gate using AC voltage.
Figure 13:
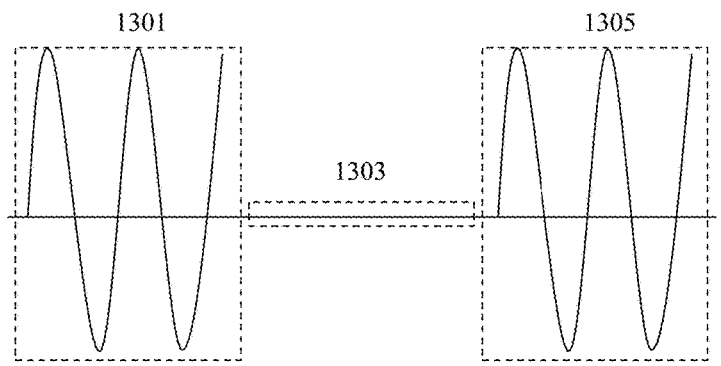
FIG. 13 shows the AC gate in the closed position and then completely open and then closed again.

In a variety of the embodiments, a method for operating an ion gate for a charged particle stream involves opening the ion gate by setting adjacent gate wires (grid elements) at the same potential; closing the ion gate by setting adjacent gate wires at different potentials by applying an AC voltage to the adjacent wires. The AC voltage can be controlled to provide a given frequency and amplitude that that is most suitable for the intended operation. The frequency can be a constant and/or controlled to cover a broad range during a period when the ion gate is partially open and/or closed. Similarly, the amplitude can be a constant and/or controlled in a range during a period of closing the gate. The AC voltage may be a symmetric or asymmetric waveform. The waveform can be, but not limited to: sine, square, triangle, and sawtooth. In a variety of operation modes, the AC powered ion gate can be operated as such, conducting a series of ion mobility measurements under a series of different frequencies and/or amplitudes, and then integrating the series of ion mobility measurement data into an ion mobility spectrum using common data processing algorithms, such as summing. FIG. 12 shows an example of a gate using AC voltage. Negative sample ions 1201 travel toward the ion gate wires 1205 of the gate according to the AC applied field until they come close to the gate wires where they are pulled toward the gate wires 1205 and are neutralized if the gate is not in the open state. Since AC voltage is being used to control the gate, each adjacent wire has a different polarity, which alternates between positive or negative. Therefore the gate wires 1205 are positive and are negative according to the applied AC voltage. During ion mobility measurements, the ion gate is opened for a short period of time, e.g. 100 microseconds, and then closed for a period of time, e.g. 20 millisecond, while ions are traveling in the drift tube 1208. During the closed state of the gate an ion depletion area is formed 1210. By using an AC voltage instead of a DC voltage to close the gate the ion depletion area is minimized, in particular, can be reduced by a half thereby improving the operation of the ion gate. There is little or no space charge using the AC voltage as compared to DC voltage. Since the ion gate can create tighter ion pulses when it is opened the resolution of the peaks traveling through the drift tube 1208 are significantly increased. FIG. 13 shows the AC gate in the closed position 1301 and then completely open 1303 and then closed again 1305. The open 1303 position is for a shorter period of time than that when using a DC voltage.

Figure 14:
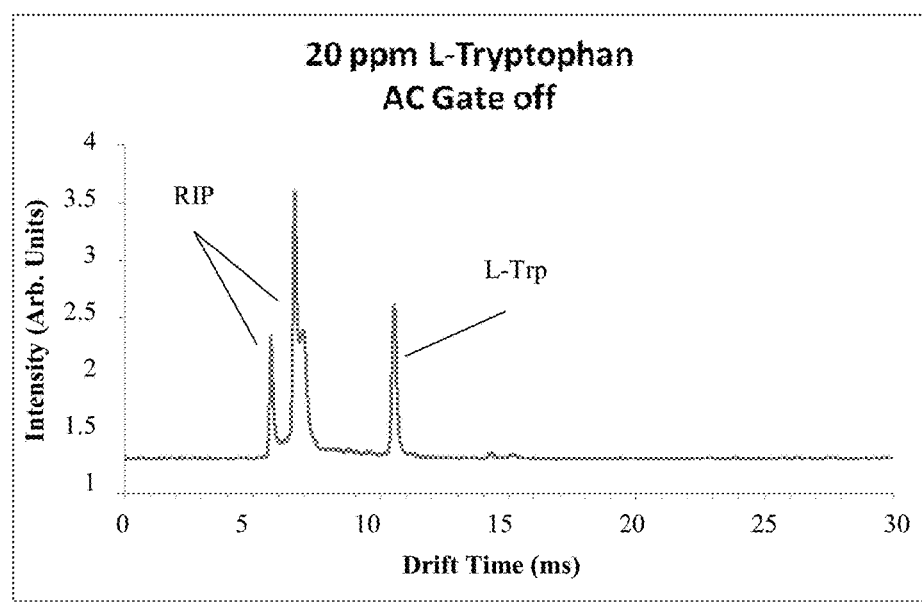
FIG. 14 shows an example of an IMS spectrum using 20 parts per million (ppm) of an L-Tryptophan sample in 80/20 methanol and water using a DC voltage on the ion gate.
Figure 15:
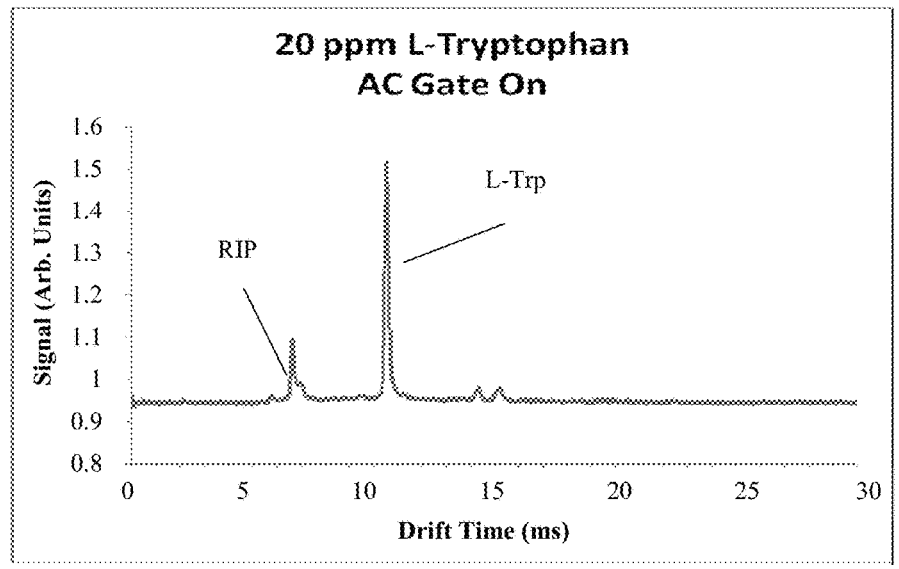
FIG. 15 shows an example of an IMS spectrum using 20 parts per million (ppm) of an L-Tryptophan sample in 80/20 methanol and water using a AC voltage on the ion gate.
Figure 16:
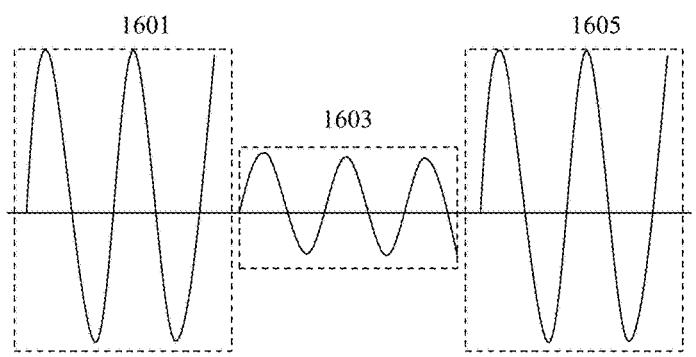
FIG. 16 shows the AC mobility selecting gate in the closed position having a voltage of 240 and then partially open having a voltage of 100 and then closed again having a voltage of 240.
Figure 17:
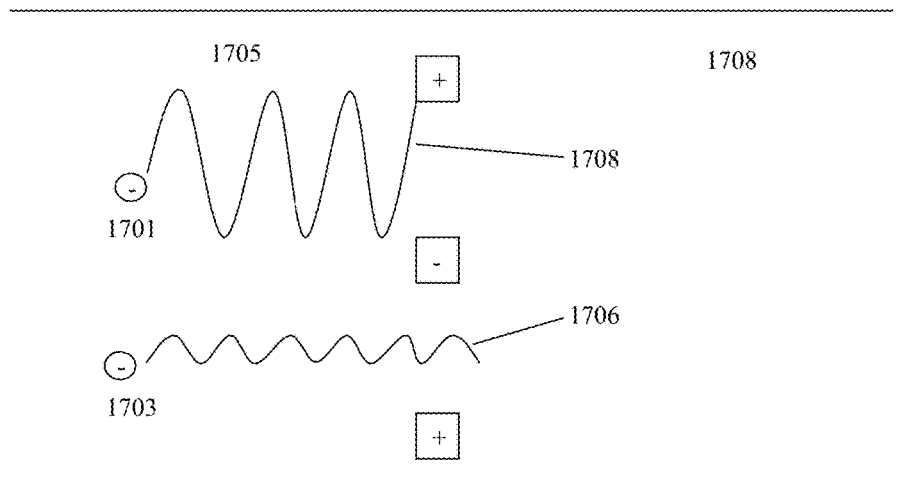
FIG. 17 shows the trajectory of ions using a 67 kHz AC frequency.

Another embodiment of the present invention is to use an AC voltage instead of DC voltage on an ion gate to filter ions according to their size and/or ion mobility. An apparatus and method is used to filter ions according to their ion mobility by varying the AC potential on a segmented Bradbury-Nielson gate. Some of the components of the charged particle stream have a smaller size and/or shape (or ion mobility) compared to the other components of the charged particle stream. The present invention controls the AC voltage on a segmented Bradbury-Nielson gate in order to filter small ions from larger ions from an ionized sample before they enter the drift tube. FIG. 14 shows an example of an IMS spectrum using 20 parts per million (ppm) of an L-Tryptophan sample in 80/20 methanol and water using a DC voltage on the ion gate. The reactant ion peak (RIP) and L-Tryptophan (L-Trp) are shown as peaks in the spectrum. When AC voltage is used on the ion gate smaller sized ions such as the RIP peaks can be substantially eliminated as shown in FIG. 15. The AC frequency can be tuned to control the specific ion mobility that is excluded from being transmitted from the ionized sample into the drift tube. For example, an AC frequency of 67 kHz and a 100-240 voltage range between the gate wires would exclude small ions having a 100 molecular weight size from the other ions in the sample that have a larger molecular weight greater than 100. FIG. 16 shows the AC mobility selecting gate in the closed position 1601 having a voltage of 240 and then partially open 1603 having a voltage of 100 and then closed again 1605 having a voltage of 240. In this mode, when the gate is open 1603, only larger molecular weight (low ion mobility) components of the sample can get through the gate without getting neutralized on the gate wires. The AC mobility selecting gate works by tuning the AC frequency in the reaction region (desolvation region) 1705 as shown in FIG. 17. When components of a sample have different ion mobilities, sizes or molecular weights, the AC frequency has a stronger or weaker effect on the components travel. For example, for two negative ions where one 701 has a molecular weight of 100 and the other ion 1703 has a molecular weight of 200 the trajectory using a 67 kHz frequency is substantially different as shown in FIG. 17. The smaller (high mobility) ion 1701 has a larger oscillation 1708 than the larger (low mobility) ion's oscillation 1706. When the AC gate is only partially open as in FIG. 16 the larger ion 1703 passes the gate wires onto the drift tube 1708 and the smaller ion 1701 is neutralized on the gate wire.

Figure 18:
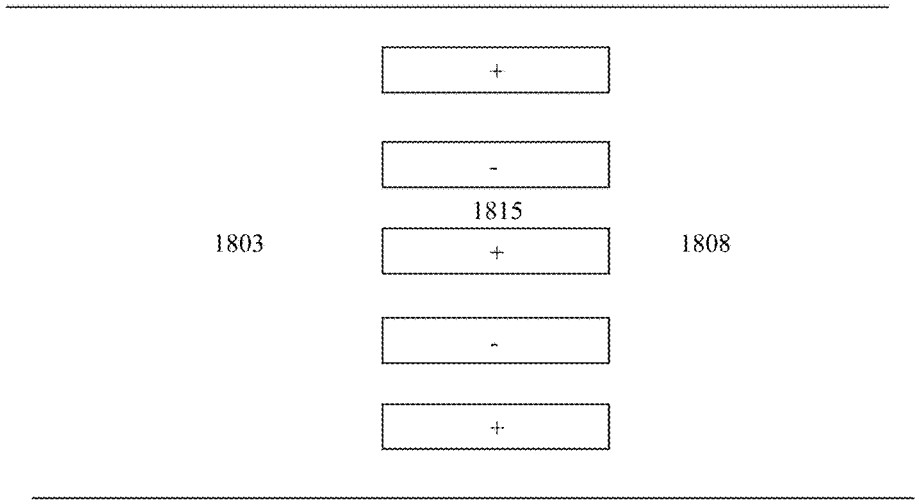
FIG. 18 shows gate wires that have a large surface area.
Figure 19:
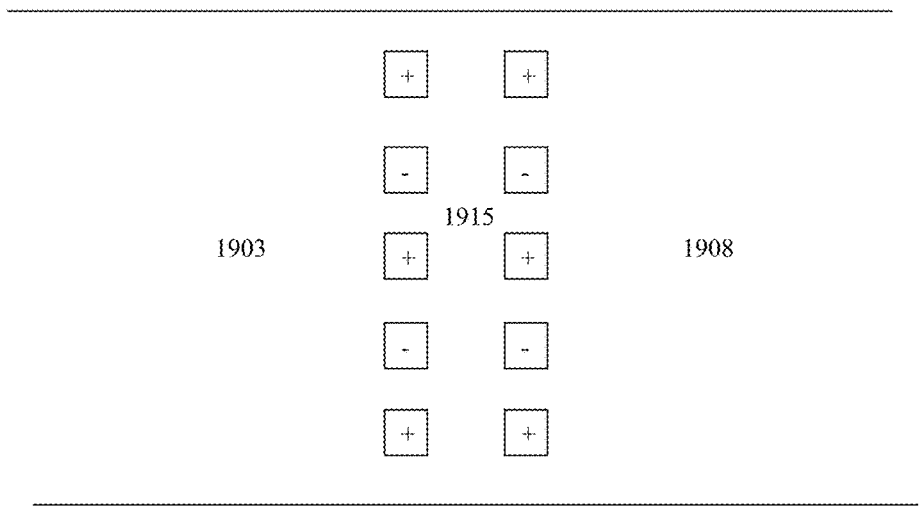
FIG. 19 shows 2 sets of gate wires aligned in phase.
Figure 20:
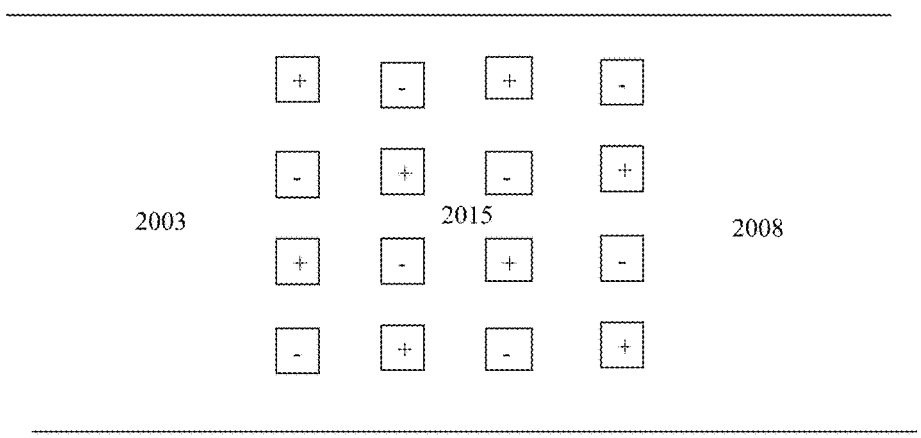
FIG. 20 shows 4 sets of gate wires in an array that are out of phase.

In yet another embodiment, the wires of the AC gate can be configured to enhance the size selection. As shown in FIG. 18, the wires 1815 can be made rectangular such that certain small ions would have a larger surface area in the direction that is parallel to the charged particle stream to be neutralized on and the frequency tuning could be established such that the small and large ions are within a few molecular weight units and still be differentiated. Alternatively, the wires 1815 in FIG. 18 can be 2 or more that are aligned in phase as shown in FIG. 19 or 2 or more are out of phase in any array as shown in FIG. 20. When 2 or more wires are used in an array that are out of phase a specific component ion mobility can be filtered out thereby letting the other components through the gate. The configuration shown in FIG. 20 provides the ability eliminate one specific sample component from traveling through the gate to the drift tube 2008. This is different from other configurations where they operate as a cut-off whereby all small size and/or shape ions are eliminated at a certain point. In a variety of the embodiments, a method for operating an AC ion gate for charged particles stream involves; applying an AC voltage to 2 or more wires; the AC voltage are out of phase, selectively eliminating one or more sample components from the charged particle stream while partially opening the ion gate; conducting ion mobility and/or mass measurement. The operating method may further include applying a series of AC voltages in certain sequence during ion mobility measurement. Such sequence may include AC voltage that selectively eliminating sample component ions in the charge particle stream from high ion mobility to low ion mobility; or from low mobility to high mobility; or selectively for one or more targeted sample components with certain ion mobilities. The frequency and/or amplitude of the AC voltages in such sequence may be altered in a continuous or discrete fashion.

In a variety of the embodiments, a method for operating an AC ion gate for a charged particle stream involves; applying an AC voltage to one or more of the gate wires to partially open and/or close the ion gate, partially opening the ion gate with an AC voltage that is greater than 0 but less than the AC voltage used to close the ion gate, and filtering a percentage of some components of the charged particle stream from the other components of the particle stream by neutralizing such components on the ion gate wires. The frequency and/or amplitude of the AC voltage can be controlled in a range or held constant during a period of closing the gate. The AC voltage can be a symmetric or asymmetric waveform. The percentage of some components of the charged particle stream being filtered from the other components can be 0 to 100%, in particular, 100%, greater than 75%, greater than 50%, greater than 25%, greater than 10%, or a small percentage being greater than 0%.

In one embodiment, the method of operating an AC gate may include a series of pulse of ions that allow different components of charged particle stream to pass through the AC gate; and analyze the components of charged particle stream based on their ion mobility and/or mass to charge ratio.

In one preferred embodiment of a time of flight ion mobility spectrometer include an ionization source located on one end of the ion mobility spectrometer is used to ionize the samples. An electric field is used to guide the ionized sample toward an ion gate. On the ion gate, at least one AC voltage is applied to the gate elements where at least one pulse of the ionized sample is passed into a drift tube. The ionized sample is then guided by another electric field to guide the pulse(s) of ions toward an ion detector. The ion detector is commonly located at the other end of the spectrometer. The AC voltage can be composed using one or more waveform. The AC voltage has a waveform that is substantially same as the asymmetric waveform used in differential/field asymmetric ion mobility spectrometers, an example of such waveform is shown in FIG. 21. The time of flight ion mobility spectrometer can offer two separation mechanisms in one integrated structure. The ionized sample mixture is first filtered by the AC ion gate based on their ion mobility differential under high electric field condition between grid elements; only selected ions under a given AC voltage condition can pass the ion gate as a pulse of ions, and then, the pulse of ions are further separated ion the drift tube of the time of flight ion mobility spectrometer based on their low field ion mobility. The AC gate can sweep through a range of AC voltages to select ions with different high field mobility to be pulsed into the drift tube for further separation. With this measurement, a 3D separation plot could be generated with one axis of low field ion mobility, or drift time, and another axis of compensation voltage of the asymmetric waveform for DMS/FAIMS, and the third as axis of ion intensity.

Even though many embodiments and examples given in this disclosure refer to ion gate for general IMS device, these devices can be operated under low vacuum, ambient or high pressure conditions. Alternatively, the ion gate can be operated in liquid for liquid phase IMS or other devices, such as electrophoretic devices, where packets of ions need to be formed. The ion gate can also be used under vacuum conditions for generating ion packets for mass spectrometers, such as a time of flight mass spectrometer. This invention discloses gating methods and apparatuses that can be used for any device where packets of charged particles need to be formed.

In various aspects, the present invention provides multi-dimensional ion mobility spectrometry (MDIMS) systems, preferably with multi-dimensional electric field designs in one integrated spectrometer, and methods of operating such systems. In various embodiments, the MDIMS systems and/or methods provide improved sensitivity and resolution compared to conventional single dimension drift tubes. In various embodiments, improved sensitivity can be achieved by using the first dimension as an ion storage region to improve system duty cycle. In various embodiments the MDIMS systems and/or methods provide improved mobility resolution. In various embodiments, improvements can be achieved by the use of drift regions which can further separate ions that are or have already been separated based on their mobilities. In various embodiments, as ion species are being separated in the first dimension, the columbic repulsion among them is reduced by transferring them to a second IMS dimension (e.g., using a kickout pulse). Thus, in various embodiments, higher mobility resolution can be experienced in the second dimension. In various embodiments, the first dimension can be used as an ion reaction region where further ion conversion can be achieved. In various embodiments of a MDIMS, and appropriate electric field application, a MDIMS can be used to detect both positive and negative ions substantially simultaneously.

In various embodiments of the MDIMS, it is understood that a preferred embodiment is to arrange the drift axis of each dimension in orthogonal geometry, however, the drift axis can be arranged in parallel, anti-parallel or with an angle in between to achieve similar results.

It is to be understood, that the electrical drift field strength-to-gas number density ratio (E/N value, often expressed in units of Townsend) in all IMS dimensions of the present MDIMS apparatus and methods is chosen to establish a steady-state drift environment, sometimes referred to as a low field environment.

With the MDIMS of the present inventions, the ion mobility spectrum can be represented, e.g., in a 2-D or 3-D plot, and can use a non-linear detection window. Chemicals can be identified in their 1-D, 2-D or 3-D mobility profile. This mobility profiling method can provide additional information and thus, can provide greater confidence for chemical (e.g., explosive) identification.

In various embodiments a Dual Polarity Ion Extraction (DPIE) operational mode can be conducted using the first dimension as a flow through cell where both positive and negative ions are brought into the first drift chamber by gas flow while the drift voltage in the first dimension is turned off (i.e., substantially no drift field is present). At a predetermined time ions are and kicked out into the second dimension, preferably such that the positive and negative ions in the first dimension are substantially simultaneously extracted into two separated drift chambers in the second dimension. After ions are separated in the second dimension, they can be further separated and detected in the third or higher dimensions.

In various embodiments, ionized samples are guided into and/or formed in the first drift region and subject to a first order separation based on mobility (resembling conventional IMS). At a given predetermined time, separated ions in the first dimension (first drift tube) are kicked out into the second drift dimension drift region where they are separated in the direction that is substantially perpendicular to the first drift direction. The same process can be continued in the higher dimensions if desired with further dimensions of IMS.

In one embodiment, the three walls in the first dimension are at 1,000 V and the gate grids are set at 0 V and 2,000 V respectively. The sample gas flow used to carry ions through the first dimension can be exhaust, e.g., behind the first dimension detector. After ions are separated in the second dimension, a kick out voltage can be applied to bring the separated ions into the third dimension. In a continuous sample detection scenario, the sequence will repeat. For a chemical mixture that may form both positive and negative ions, various embodiments of the DPIE technique can extract more than 50% of both positive and negative ions into the second dimension.

In various embodiments, the MDIMS devices can transport ions between each dimension without significantly losing resolving power. In various embodiments, when ions are separated in the first dimension; they can look like a thin plate. To move them into the direction that is perpendicular to the first dimension, voltages are changed on the appropriate electrodes (typically an electrode opposite the inlet, the inlet itself, or both) within a microsecond range. The electric field during these kick out moments can be manipulated to create temporary high and low electric field zones. The thin plate in the high field zone can be compressed into a thin line in the low field zone of the second dimension.

In various embodiments, a MDIMS comprises an ionization source to, for example, (a) generate reactant ions and a reaction region where reactant ions can react with samples and form product ions to be detected for sample identification; (b) generate sample ions for detection, (c) or both. The reaction region can be guarded by ion guides that generate a substantially continuous electric field to, e.g., lead the ions to the first dimension drift region (first drift tube).

In Multiple Step Separation (MSS) mode operation, a pulse of ions are generated by opening an ion gate, to introduce them into the first dimension drift region; the ions are separated based on their mobilities under the guidance a substantially continuous electric drift field in the first drift tube. In one embodiment, the electric field is generated by a series of ion guides. Each ion guide can comprise one or more electrodes; and different voltages can be applied on each electrode to establish the potential difference across the first drift tube. For example, four electrodes can be used for each of the first dimension ion guides.

In various embodiments of MSS mode operation, as a first group of ions reaches the first dimension detector matrix, a kick out voltage can be applied to generate a high electric field that is perpendicular to the first dimension drift field, thus the ions separated in the first dimension are moved into the second dimension drift region. An electric field separator screen can be used to help define the electric field in the second dimension. Ions introduced into the second field will continue to drift across the second dimension drift region and further separation can be achieved. The ion guides in the second dimension can be arranged similarly to the first dimension ion guides, for example, if a third dimension of separation is desired. If a third dimension is desired, complete square electrodes can be used as the ion guides. Ions separated in the second dimension can be detected by the detector. The detector can comprise multiple detectors according to required special resolution of the spectrometer or a single detector.

In various embodiments, a partial kick out operation can be performed when ions are introduced from the first dimension to the second dimension. If only a portion of the ions are kicked out, the mobility measurement in the first dimension can be resumed after the kick out. Thus, an ion mobility spectrum can also be acquired independently in the first dimension. As a complete kick out can increase the sensitivity in the second dimension, alternating between these operation methods can be beneficial. In addition, a clean up operation, e.g., remove all ions in the drift chambers by an applied "kick out" electric field for an extended period of time, can also be added between detection cycles.

The low dimension operation of the spectrometer can be used as fast screening method to generate a quick survey of the ionic species from the ionization source. In combination with the normal operation of the MSS mode, the survey of the ionic species can be used as an index to guide upper dimension operations. The survey mode operation can also be used to selectively kick out ions of interest, simplifying higher dimension spectra, and saving total analysis.

Different drift/separation conditions can be established independently for each dimension, e.g., different drift gases may be used in each dimension or different drift gas temperatures in each dimension.

The MDIMS can be operated in a fashion where a number of multiple dimensional positive ion mobility data is collected followed by a number of multiple dimensional negative ion mobility data. The sequence can be realized, e.g., by alternation the polarities of electric fields in the spectrometer.

During MSS mode operation, the directions of the drift gas flow can be set to be counter to or across from the ion movement. The size of each gas port can be selected depending on the flow required to achieve the flow pattern inside the spectrometer and preferably the drift flow sweeps the entire drift region and removes excessive sample molecules and any other reactive neutral molecules.

Figure 22:
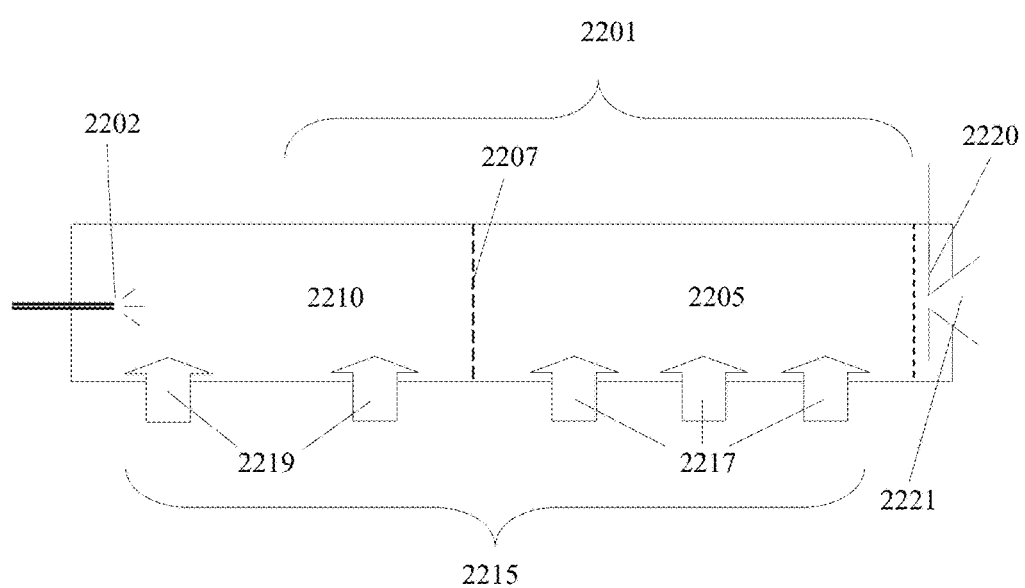
FIG. 22 shows an IMS using a cross-flow drift medium design.

One aspect of the present invention is a method and apparatus for using a cross flow IMS apparatus for effectively removing neutral molecules from drift tube. In a time of flight type ion mobility spectrometer, the cross gas flow is used in a manner that is similar to conventional uni- or counter-directional drift gas flow, the drift gas flow does not substantially affect the ion separation along the drift axis. Compared to prior art counter- and uni-direction drift flow design, the cross flow design allows neutral molecule(s) to only travel a short distance and less time in a drift region. A non-limiting example is shown in FIG. 22 where a drift segment is used. However more than one drift segment can be used. The drift tube 2201 comprises: an ionization source 2202, a desolvation region 2210 and an analytical segment (drift region) 2205 separated by an ion gate 2207. After a sample is introduced into one end of the IMS (in this particular case an ESI source 2202 is used; any other ionization source could be used), the ionized sample and solvent ions are formed in the desolvation region 2210, a narrow pulse on the ion gate 2207 introduces the ion mixture into the separation segment 2205. This configuration has the drift gas flow 2215 (comprised of drift flow for desolvation 2219 and separation 2217) in a direction that is substantially perpendicular to the drift axis of the ions; the drift axis generally represent the averaged ion path in the drift tube. With cross flow configuration, neutral molecules that travel with the drift and desolvation gas flow are not mixed across desolvation and drift region. Neutral fragments that are generated during drift and desolvation process in the drift tube are effectively removed from the drift tube avoiding further gas phase ion molecular interaction in the drift tube. The cross-directional drift gas can be in a direction that is between greater than 0° to less than 180° to that of the drift axis of the ions. The cross-directional drift gas is applied to a substantial portion of the desolvation and/or drift region. In many cases the cross-directional drift gas is applied over the entire drift axis. In addition, the cross-directional gas flow 2215 can be a drift medium that comprises various components. The components may be a plurality chemical modifiers and/or a plurality of drift gases. The cross-directional flow can comprise different drift medium in the different segments and/or regions of the IMS. For example, as shown in FIG. 22, drift gas flow 2219 can comprise the same and/or different drift medium as drift gas flow 2217.

In various embodiments, the cross flow configuration for the IMS can be combined with counter or uni-direction flow configurations. For example, if the drift region has a cross flow arrangement as shown in FIG. 22, a portion the drift flow could be exhausted into the desolvation region and then pumped away from the end of the desolvation region, given the desolvation region is using a counter direction gas flow arrangement.

Figure 23:
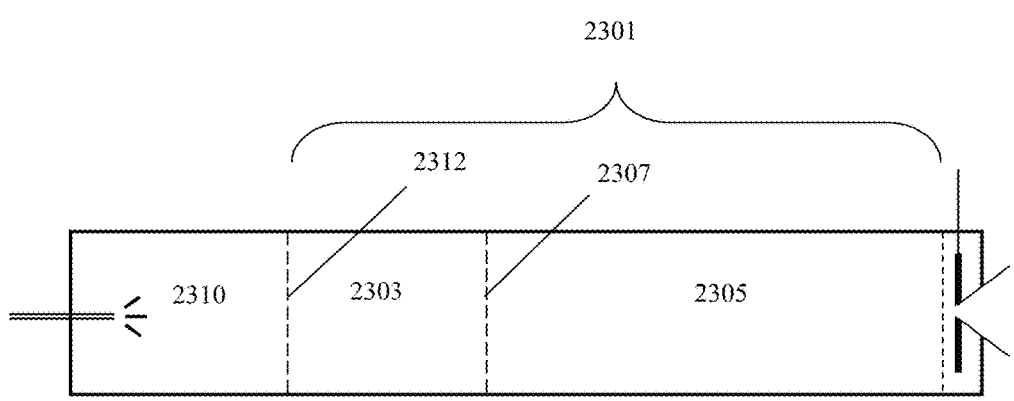
FIG. 23 shows an IMS using a segmented drift tube for pre-separation.

In another aspect of the present invention a multiple segmented IMS apparatus is used for pre-separation of the sample. A non-limiting example is shown in FIG. 23 where two drift segments are used. However more than two drift segment can be used. The drift tube 2301 comprises: a pre-separation segment 2303 and an analytical segment 2305 separated by an ion gate 2307. The pre-separation segment 2303 resembles the pre-separation column used in chromatography. After a sample is introduced into one end of the IMS (in this particular case an ESI source is used, any other ionization source could be used), the ionized sample and solvent ions are formed in the desolvation region 2310, a narrow pulse on the first ion gate 2312 introduces the ion mixture into the pre-separation segment 2303. The second ion gate 2307 is timed to open so that only components of the sample are allowed to enter the analytical segment 2305. Elimination of the solvent avoids ion-molecule reactions in the analytical segment 2305 of the drift tube 2301.

In the various embodiments the two gate IMS apparatus and method, the first gate transmits packets of ions and these ions move to the second gate. Part of the ions from the first gate will be transmitted through to the second gate and the transmitted ions will be further separated through the drift region. Ions at the second gate have low density and the space charge effect can be reduced and the IMS will have enhanced separation. The IMS separated ions can be detected by a faraday plate and can be transported to a mass analyzer for further analysis.

In another embodiment of the two gate IMS apparatus and method, the first gate transmits narrow ion packets. Higher ion mobility ions take a shorter time to get to the second gate than lower mobility ions. By controlling the second gate timing, certain mobility ions are transmitted through the second gate. The first gate can be controlled to transmit the second, third, fourth, etc. ion packet before the first packet reaches the detector. The first and second gate will be operated synchronously with different start-on time and width of opening. Ions transmitted through the second gate will be separated while traveling through the drift region and being detected by the detector or being transported to the mass analyzer. The first gate opening will have a specific period which was determined not to mix ions of different packets. A grid in front of the detector can be replaced by an exit gate to further limit the ions with specific ion mobility.

A segmented drift tube with multiple ion gates can be used with cross flow design for easy application of different drift media in different segments, however, segmented drift tube design could be used with one drift media, and/or with conventional uni- or counter-direction drift gas flow designs.

Figure 24:
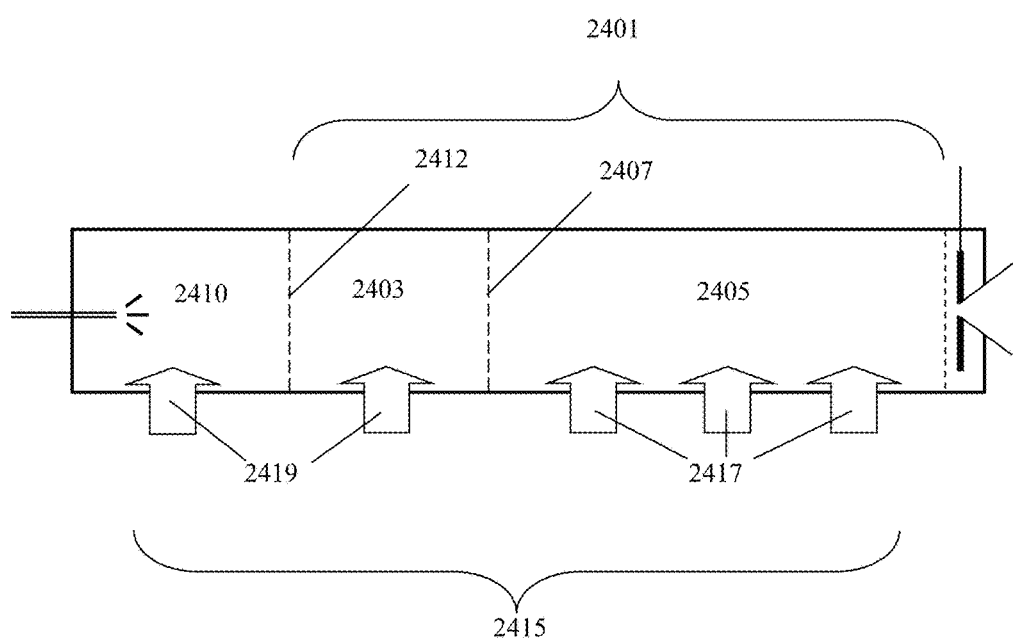
FIG. 24 shows an IMS using a cross-flow drift medium design combined with a segmented drift tube.

In another aspect of the present invention a multiple segmented planar IMS apparatus combined with a cross flow can be used to enhance separation of components of a sample. In this case, solvent ions as well as solvent neutrals are eliminated from the analytical segment. A non-limiting example is shown in FIG. 24 where two drift segments are used. However more than one drift segment can be used. The drift tube 2401 comprises: a pre-separation segment 2403 and an analytical segment 2405 separated by an ion gate 2407. The pre-separation segment 2403 resembles the pre-separation column used in chromatography. After a sample is introduced into one end of the IMS (in this particular case an ESI source is used, any other ionization source could be used), the ionized sample and solvent ions are formed in the desolvation region 2410, a narrow pulse on the first ion gate 2412 introduces the ion mixture into the pre-separation segment 2403. The second ion gate 2407 is timed to open so that only components of the sample are allowed to enter the analytical segment 2405. Elimination of the solvent avoids ion-molecule reactions in the analytical segment 2405 of the drift tube 2401. This configuration has the drift gas flow 2415 in a direction that is substantially perpendicular to the drift axis of the ions, the drift axis generally represent the averaged ion path in the drift tube. With cross flow configuration, neutral molecules that travel with the drift and desolvation gas flow are not mixed across desolvation and drift region. Neutral fragments that are generated during drift and desolvation process in the drift tube are effectively removed from the drift tube avoiding further gas phase ion molecular interaction in the drift tube. The cross-directional drift gas can be in a direction that is between greater than 0° to less than 180° to that of the drift axis of the ions. The cross-directional gas flow can be a drift medium that comprises various components. The components may be a plurality chemical modifiers and/or a plurality of drift gases. The cross-directional flow can comprise different drift medium in the different segments of the IMS. For example, as shown in FIG. 24, drift gas flow 2419 can comprise the same and/or different drift medium as drift gas flow 2417.

A separation apparatus, comprising: an ionization source ionizing a sample that contain a least one component in front of an ion gate; a drift tube that has a drift axis along which ions are separated; and a drift flow in a direction that is greater than zero but less than one hundred and eighty degrees from the drift axis. The apparatus can further comprise at least one chemical modifier that is added to the drift flow for separation enhancement. In one embodiment, a separation apparatus comprising: an ionization source ionizing a sample that ionizes samples; a drift tube has a drift axis along which ions are separated, wherein the drift tube has greater than or equal to, two drift segments in which the ions are separated, and a ion gate that is placed between drift segments. The separation apparatus may further comprises at least one chemical modifier that is added to the drift flow.

In another embodiment of the present invention, a chemical modifier can be added to different segments or regions of the IMS in order to target specific interactions with various components of the sample. Two or more segments can be used, but for simplification a two segment design will be discussed. Therefore two or more different chemical modifiers can be used in the IMS without substantially interfering with each other. 0 to 100% of modifier can be used in each of the different segments or regions of the IMS. The cross flow drift design is one way to add the modifier, but it is not necessary to use cross flow in order to add the modifiers to each segment or region in the IMS. The different segments or regions can be isolated from each other by a number of ways which include but are not limited to; using gates in between or a small opening, slits or pinholes. In this configuration, a modifier that targets one functional group can be added to the first region of the IMS and a second type of modifier can be added to the next region that interacts with a different functional group. Unlike previous methods where a transforming agent, immobilizing agent, or chiral molecule is added to the sample components prior to ionization, in this process, the sample components are modified in the drift tube in discrete sections according to the desired interaction. For example, in order to separate a pair of enantiomers in a sample, a chiral modifier added to the cross flow drift gas in the first region of the drift tube which forms diastereomer components that are then interacted by a second modifier added to the cross flow drift gas in a second region of the drift tube to enhance separation.

Figure 25:
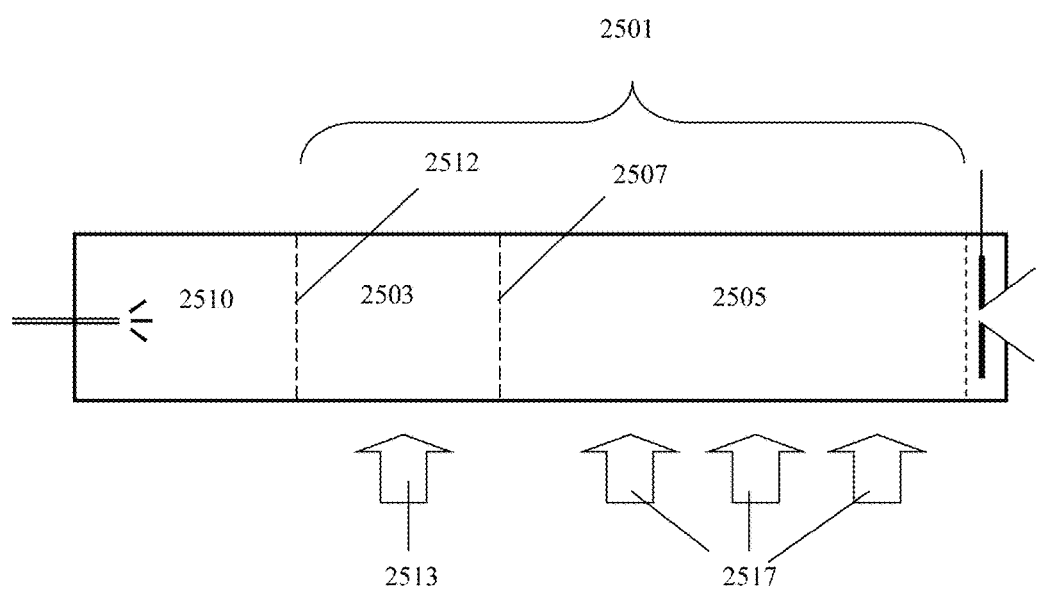
FIG. 25 shows an IMS using a segmented drift tube design with cross flow for adding specific modifiers to each segmented region.

FIG. 25 shows an IMS where the sample is ionized in the desolvation region 2510. The drift tube 2501 consists of two regions 2503 and 2505 that have an applied electric field (not shown) and are separated by a gate 2507. Another gate separates the desolvation region 2510 from the drift tube 2501 with a gate 2512. In the case of a sample that has two enantiomer components, this enantiomer pair is ionized in the desolvation region 2510 and is then allowed to travel into the first separation region 2503 whereby 0-100% of a chiral modifier is added to the cross drift flow 2513 which interacts with the enantiomer pair. Diastereomers are then formed and are let into the second separation region 2505. These diastereomers are then separated in the second separation region with enhanced separation by using 0-100% of a modifier that is added to the cross drift flow 2517.

One embodiment of this invention is to rigidify the molecules (limit the number of conformations) by adding an immobilizing agent to the first drift region of the drift tube. The immobilizing agent stabilizes the gas phase structure of analytes in order to enhance the interaction of the modifier in the second region of the drift tube in order to enhance separation. In variety of embodiments, a modifier that can frame (affix) the higher order structure of a gas phase analyte molecule is used to achieve well-defined gas phase mobility of the analytes. Forming complexes with metals and/or other molecules is a non-limiting example of this method. Another embodiment of this invention is to add at least one transforming agent as a modifier to the first drift region, which bonds/binds (interacts) to at least one component of the sample. The bonding interactions or attraction forces may include; hydrogen bonds, van der Waals forces, dipole-dipole, steric hindering effects, coordinate covalent bond, metallic bond, ionic bond, non-covalent bond, covalent bond, weak covalent nature, antibonding, short-lived metastable, clusters, but is not limited to only these. A second chemical modifier is added to the second region of the drift tube that interacts selectively with the component of the sample and/or transforming agent which resolves/separates the component from other components of the sample based on their measured ion mobility characteristics.

Figure 26:
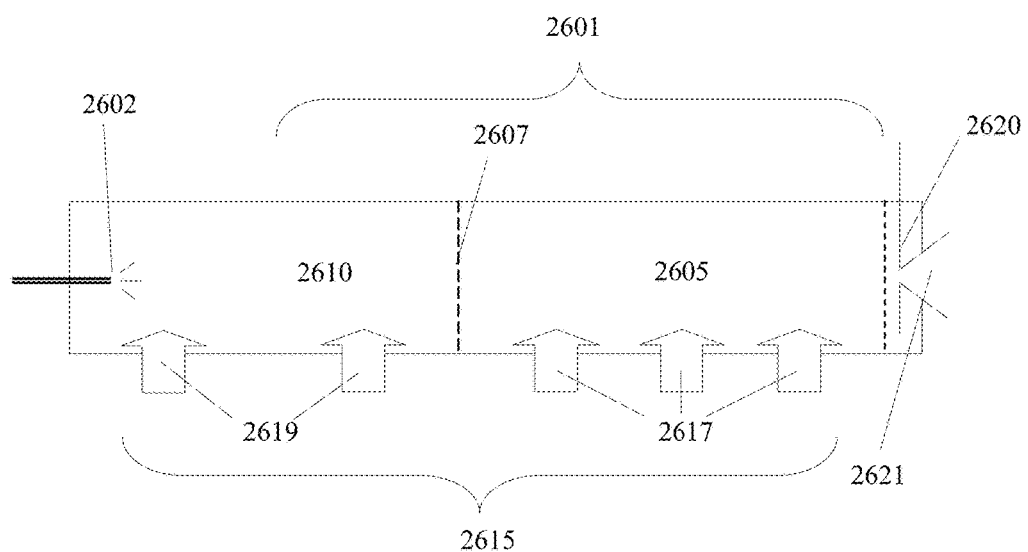
FIG. 26 shows an IMS using a drift tube design with cross flow and with an AC gate.

When using a modifier, the modifier can interact with solvent ions and for additional ions; the modified solvent ions can overwhelm the signal from the ions of interest. By using an AC gate, this invention allows the removal of the solvent ions before the drift tube separation region where the modifier is introduced to. A non-limiting example is shown in FIG. 26 where a drift segment is used. However more than one drift segment can be used. The drift tube 2601 comprises: an ionization source 2602, a desolvation region 2610 and an analytical segment (drift region) 2605 separated by an AC ion gate 2607. After a sample is introduced into one end of the IMS (in this particular case an ESI source 2602 is used; any other ionization source could be used), the ionized sample and solvent ions are formed in the desolvation region 2610. The AC gate 2607 is operated to reject the low molecular weight solvent ions, and a pulse on the AC ion gate introduces the rest of the ion mixture into the separation segment 2605. This configuration has the drift gas flow 2615 (comprised of drift flow for desolvation 2619 and separation 2617) in a direction that is substantially perpendicular to the drift axis of the ions; the drift axis generally represents the averaged ion path in the drift tube. The cross-directional drift gas can be in a direction that is between greater than 0° to less than 180° to that of the drift axis of the ions. The cross-directional drift gas is applied to a substantial portion of the desolvation and/or drift region. In many cases the cross-directional drift gas is applied over the entire drift axis. In addition, the cross-directional gas flow 2615 can be a drift medium that comprises various components. The components may be a plurality chemical modifiers and/or a plurality of drift gases. The cross-directional flow can comprise different drift medium in the different segments and/or regions of the IMS. For example, as shown in FIG. 26, drift gas flow 2619 can comprise the same and/or different drift medium as drift gas flow 2617.

In another embodiment, the AC ion gate 2607 is operated as FAIMS (DMS) device, for example, using elongated gate elements as shown in FIG. 18 and applying a waveform such as the example shown in FIG. 21. In this embodiment, a pulse of ions that are characterized by a single FAIMS compensation voltage are allowed through the AC gate; these ions are then separated in the drift region 2605. This configuration has the drift gas flow 2615 (comprised of drift flow for desolation 2619 and separation 2617) in a direction that is substantially perpendicular to the drift axis of the ions; the cross-directional drift gas can be in a direction that is between greater than 0° to less than 180° to that of the drift axis of the ions. The cross-directional drift gas is applied to a substantial portion of the desolvation and/or drift region, or over the entire drift axis. In addition, the cross-directional gas flow 2615 can be a drift medium that comprises various components. The components may be a plurality chemical modifiers and/or a plurality of drift gases. The cross-directional flow can comprise different drift medium in the different segments and/or regions of the IMS. For example, as shown in FIG. 26, drift gas flow 2619 can comprise the same and/or different drift medium as drift gas flow 2617.

An ion mobility spectrometer apparatus can have an ionization source that is in fluid communication with a drift tube; an AC ion gate that located between the ionization source and the drift tube pulses a group of ions into the drift tube where the group of ions are separated along a drift axis, and at least one drift gas that flows substantially in a direction that is greater than zero but less than one hundred and eighty degrees from the drift axis. The group of ions are pre-separated by an AC ion gate comprising applying at least one AC voltage to at least one of the grid elements of the AC ion gate to pass a pulse of selected ions into the drift tube. The AC voltage has an asymmetric waveform as used in an DMS. the drift gas can also use different drift gases or by adding chemicals into the drift gas. The drift tube is a segmented drift tube. The group of ions are pre-separated by a previous section of a segmented drift tube. The segmented drift tube is divided by the AC gates positioned between each segments only allowing selected ions to pass the ion gates. The segment of the drift tube uses different gas compositions. The group of the ions is a mixture of solvent(s) and sample(s). The pre-separation is to eliminate solvent ions for the group of ions.

An ion mobility spectrometer method can be operated by forming ions in an ionization source that is in fluid communication with a drift tube; pulsing a group ions that into a drift tube; separating the group of ions along a drift axis of the drift tube, and; providing at least one drift gas that flows substantially in a direction that is greater than zero but less then one hundred and eighty degrees from the drift axis. The group of ions are pre-separated by an AC ion gate comprising applying at least one AC voltage to at least one of the grid elements of the AC ion gate to pass a pulse of selected ions into the drift tube. The AC voltage has an asymmetric waveform as used in an DMS. The drift gas further comprises adding chemicals into the drift gas. The drift tube is a segmented drift tube. The group of ions are pre-separated by a previous section of a segmented drift tube. The segmented drift tube are divided by the AC gates positioned between each segments only allowing selected ions to the ion gates. Each segment of the drift tube uses different gas compositions. The group of the ions is a mixture of solvent(s) and sample(s). The pre-separation is to eliminate solvent ions.

A separation method, comprising ionizing a sample with at least one component; separating the ionized sample along a drift axis of a drift tube, and proving a drift flow in a direction that is greater than zero but less than one hundred and eighty degrees from the drift axis. The separation method may further comprise removing neutral molecules in the drift tube along with the drift flow; the neutral molecules could be, but not limited to, one component of the sample; fragment of a sample molecule; contaminants in the apparatus. In one embodiment, a separation method comprising: ionizing a sample with at least one component; providing the sample to an ion mobility based spectrometer with greater than or equal to, two drift segments separated by an ion gate between the drift segments; transporting the ionized sample as a ion packet along a drift axis; and pre-separating the ion packet in one of the drift segments prior to further separation in other separation segments. This separation method may further comprises; adding at least one chemical modifier to a drift gas flow that is in a direction to that of the drift axis of the ions that is between greater than 0 degrees to less than 180 degrees.

In various embodiments, the drift gas can be supplied to the higher dimension in the direction that is in substantially parallel to the lower dimension. Under linear flow conditions and the parallel flow pattern, for example, limited mixing of drift gas near the dimension interface is expected.

In SBA mode operation, the sample is provided into the spectrometer through an inlet port. Through the ionization source, the ionized the samples are brought into the first dimension drift region by gas flow. In various embodiments of the SBA operational mode, the first dimension drift tube can be used as ion storage device to, e.g., increase the duty cycle of the device.

In various embodiments of Continuous First Dimension Ionization (CFDI) mode operation, the samples are introduced to the spectrometer as pulses of gas. The sample gas pulse can be formed in a wide variety of ways, for example, by thermally desorbing chemicals from a surface, as the eluent of a chromatographic separation, by pumping the sample into the spectrometer for a short period of time, introduction through a pulsed valve, etc. In many embodiments, the flow under a linear flow condition, and a "plug" of gas phase sample is directed from the inlet port towards the ionization source by gas flow. Pulses of reactant ions (preferably at high density) are generated by the ionization source and guided by the electrical drift field to drift towards the sample "plug". As the pulse of reactant ions and samples intercept in the first dimension, a portion of the samples are ionized. As the sample encounters multiple reactant ion pulses in the same acquisition period, chemicals in the sample "plug" are ionized. Chemicals with different properties (e.g., charge affinity) can thus be separated and detected at different locations on the detector matrix. This gas phase titration method can improve ionization efficiency of ion mixture where chemicals with different properties coexist. By this means chemicals that can not be detected in conventional IMS can be detected.

In various embodiments, the CFDI can also be performed in the reaction region. A plurality of pulses of reactant ion is generated by pulsing the ion gate while pulsed samples are introduced to the spectrometer from a gas port. In this implementation, the ion ion gate is removed or kept open. Pulse of ions generated in the reaction region are separated in the first dimension drift region, and then the separated ions are extracted in a higher dimension drift region for further ion mobility analysis if so desired. In various embodiments, the CFDI method can be used as an independent ionization source directly interfaced to spectrometers, such as a differential mobility spectrometer, ion mobility spectrometer or a mass spectrometer, either inline or perpendicular to the direction of the drift electric field. In embodiments where CFDI is used for a single IMS, a shutter grid will be used. The ionized chemical species continue to drift in the drift region after formation in the reaction region. Similarly, interfaces to other spectrometers, such as differential ion mobility spectrometers and mass spectrometers, can also be realized by placing the sample inlet of these instruments directly after the reaction region.

The CFDI mode can be performed using reactant ions with different chemical properties. For example, modifying the ion chemistry using a variety of chemical reagents that react with initial reactant ions can generates reactant ions with different chemical properties. These ionic species can be used, e.g., to ionize samples introduced to the spectrometer. Similar effects can be achieved, e.g., by using an ionization source that can generate different ionic species or charged particles/droplets. In various embodiments, altering the ionization chemistry can be used to achieve substantially selective ionization of targeted chemicals in the sample. For example, a series of ion pulse with different chemical properties can be used to ionize chemicals with compatible ionization properties in the sample.

In Selective Ion Introduction (SII) mode operation, one or multiple groups of selected ions are kicked out into a higher dimension. The selective kick out can be realized by applying a kick out voltage at a predetermined time to the region where ions of interests are traveling through at a given timing. In various embodiments, the kick out pulse is not necessarily applied to a selected region of the lower dimension, but the higher dimension drift chamber does not intercept the lower dimension only over a portion of length of the lower dimension; thus, e.g., a selected location can be designed only to allow a small group of ions to be kick out into the second dimension. A similar result as described with respect to MSS mode can be achieved by controlling the kick out timing and performing multiple acquisition cycles.

In various embodiments of MDIMS systems, the higher dimension drift region, such as the second dimension region, can be operated in different phases of drift media, e.g. gas or liquid. The liquid phase drift cell can be constructed with two parallel plates or grids instead of a conventional drift tube design. The liquid phase drift cell can be a thin layer of liquid that has an electric field across the layer. The higher order dimension drift cell has drift axis that is substantially parallel or substantially perpendicular to the first dimension drift axis. The higher dimension drift cell has multiple compartments (channels) that are substantially perpendicular to the lower dimension drift axis. The higher dimension drift cell can be used for selectively collecting samples separated in the lower dimension drift tube. The higher dimension drift cell can be further interface to other separation and detection apparatus, including but not limited to electrophoresis, chromatography, UV absorption and other spectroscopic apparatus.

In various embodiments of MDIMS systems of the present inventions, different drift gases are used in different drift tubes and/or dimensions of the MDIMS to separate ionic species in a higher dimension (e.g., a second dimension) that are not sufficiently separated in the drift gas in a lower dimension (e.g., the first dimension). It is to be understood that the drift gas can be a mixture of two or more gases. Similar separations can also be done by varying other drift chamber conditions.

Various embodiments that can be used to realize the SII mode operation with IMS$^n$. By reducing the physical size of the higher dimensions and controlling the timing of the kick out pulse, a selected group of ions that drifted into the kick out region can be brought into a higher dimension drift chamber where they can be further separated. The same process can be continued until the nth separation performed in different drift chambers. The geometry of the interconnected drift chambers can be two dimensional or three dimensional, thus the number of times a higher order mobility separation can be conducted is not necessarily limited by the physical space available for the spectrometer.

In various embodiments, a three dimensional MDIMS can be used for SII mode operation. When gas phase sample is introduced into the reaction region of the first dimension drift tube, between two ion gates, the sample is ionized by either CFDI or conventional ionization methods with reactant ions created by the ionization source. The sample ions mixed with reactant ions are pulsed into the first drift region. Under the guidance of the electric field generated by ion guide, the ion mixture separates in the first dimension. At a predetermined timing when ions of interest drift into the kick out region, a kick out voltage can be applied to a set of electrodes (including a split ion guide and grids) to extract ions into the second dimension. As ions are compressed in the interface between the kick out region and a second dimension drift region, narrow pulses of plural separated ions are created at the beginning of the second dimension drift region. The ions pulses are separated in the drift region that is guarded by ion guides. The further separated ions are extracted from second ion kick out region into the third drift chamber that has a drift direction that is orthogonal to the first and second dimension. The extracted ions repeat the process described above in the third dimension or higher.

In various embodiments, a MDIMS can operate in SII mode with a two dimensional structure. One peak that is isolated by the first dimension drift tube is extracted into second dimension, and then one peak isolated by the second dimension drift tube is extracted into the third dimension having a drift direction that is substantially perpendicular to the second dimension and substantially anti-parallel to the first dimension. In this example, the drift axes of all dimensions are on the same plane.

For example, in various embodiments, this configuration can be interfaced to other detectors, such as a mass spectrometer. IMS-MS systems are commonly used to achieve mobility based separation before mass analysis. The interface to a mass spectrometer can be in-line with ion drifting direction behind the detector matrix. An interface to a mass spectrometer can be through an opening on the second dimension detector matrix, or perpendicular to the drifting direction using a kick out pulse to push ions into the interface. Higher ion transportation efficiency is expected in the latter case.

In various embodiments of the MDIMS, a compact MDIMS device can be configured with three dimensions, including one first dimension chamber, two second dimension drift chambers, and two third dimension chambers, with a largest dimension of <10 cm. The configuration is to realize both CFDI and DPIE with SII mode. In CFDI operation, the reactant ions are formed in ion source and pulsed into the reaction region to selectively ionize the pulsed sample. Ionized samples are separated in the first dimension drift region and then further separated in a higher dimension drift region.

In DPIE operation, both positive and negative ions formed in the ionization source and reaction region are carried into the first dimension by carrier flow without effluence of the electric field. The positive and negative ions are extracted in to the second dimension drift chambers. The sample ions are detected on the detector matrix in the first dimension, second dimension or third dimension depending on the instrument usage and it is software controlled. For fast screening operation, ions are detected at lower dimension detectors for high throughput. For highest resolution, ions are measured at the third dimension detectors. The practical unit includes a sample inlet, a sample inlet control valve, an ionization source, and a first dimension drift region. The drift flow is designed to sweep cross the second drift region and third drift region. At the drift gas inlet, a flow distribution system is used to assure even drift flow across the entire drift chambers.

A portable system package can include a pneumatic system, electronics and computer controls, a user interface and display, battery power, and a MDIMS.

A modularized design approach is preferably used in the MDIMS of the present inventions to facilitate the provision of future upgrades. For example, a different ionization source may be desired for different applications. Such sources may be, e.g., a corona discharge, electrospray ionization or desorption electrospray ionization. The provision of a modular design can facilitate the changing of the ion source.

In another aspect, the functionality of one or more of the methods described above may be implemented as computer-readable instructions on a general purpose processor or computer. The computer may be separate from, detachable from, or may be integrated into a MDIMS system. The computer-readable instructions may be written in any one of a number of high-level languages, such as, for example, FORTRAN, PASCAL, C, C++, or BASIC. Further, the computer-readable instructions may be written in a script, macro, or functionality embedded in commercially available software, such as EXCEL or VISUAL BASIC. Additionally, the computer-readable instructions could be implemented in an assembly language directed to a microprocessor resident on a computer. For example, the computer-readable instructions could be implemented in Intel 80×86 assembly language, if it were configured to run on an IBM PC or PC clone. In one embodiment, the computer-readable instructions can be embedded on an article of manufacture including, but not limited to, a computer-readable program medium such as, for example, a floppy disk, a hard disk, an optical disk, a magnetic tape, a PROM, an EPROM, or CD-ROM (or any other type of data storage medium).

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

The claims should not be read as limited to the described order or elements unless stated to that effect. While the present inventions have been described in conjunction with various embodiments and examples, it is not intended that the present inventions be limited to such embodiments or examples. On the contrary, the present inventions encompass various alternatives, modifications, and equivalents, as will be appreciated by those of skill in the art.

It is recognized that modifications and variations of the invention disclosed herein will be apparent to those of ordinary skill in the art and it is intended that all such modifications and variations be included with the scope of the appended claims.

What is claimed is:

1. An ion mobility spectrometer apparatus, comprising:
An ionization source that is in fluid communication with a drift tube;
An AC ion gate, in which at least one power supply applies at least one AC voltage to at least one grid element of the AC ion gate, where the AC ion gate is located between the ionization source and a drift region of the drift tube, and pulses a group of ions into the drift region where the group of ions are separated along a drift axis of the drift region; and
At least one drift gas that flows substantially in a direction that is greater than zero but less than one hundred and eighty degrees from the drift axis.

2. The apparatus of claim 1, wherein at least one power supply applies an AC voltage waveform to the AC ion gate that causes the group of ions to be pre-separated by the AC ion gate before entering into the drift region.

3. The apparatus of claim 2, wherein the AC voltage waveform that causes the group of ions to be pre-separated is a waveform that eliminates solvent ions from the group of ions before the group of ions enter into the drift region.

4. The apparatus of claim 1, wherein at least one power supply applies an AC voltage to the AC ion gate that has an asymmetric waveform as used in a DMS and/or FAIMS.

5. The apparatus of claim 1, further comprises chemical modifiers that are added into the drift gas.

6. The apparatus of claim 1, wherein the drift tube is a segmented drift tube.

7. The apparatus of claim 6, wherein the segmented drift tube is divided by multiple AC gates positioned between pairs of adjacent segments, with each of the AC ion gates only allowing selected ions to pass that AC ion gate.

8. The apparatus of claim 6, wherein the group of ions are pre-separated by a section of the segmented drift tube prior to the AC ion gate.

9. The apparatus of claim 6, wherein different segments of the drift tube contain different gas compositions, including different gases and/or chemical modifiers.

10. An ion mobility spectrometer method, comprising:
Forming ions in an ionization source that is in fluid communication with a drift tube;
Pulsing a group of ions into a drift region of the drift tube using an AC ion gate;
Separating the group of ions along a drift axis of the drift region; and
Providing at least one drift gas that flows substantially in a direction that is greater than zero but less than one hundred and eighty degrees from the drift axis.

11. The method of claim 10, wherein the group of ions are pre-separated by an AC ion gate before entering into the drift region.

12. The method of claim 10, further comprising using the AC ion gate to separate and/or filter some of the ions in the group of ions by applying an asymmetric waveform as used in a DMS and/or FAIMS.

13. The method of claim 10, further comprises adding chemical modifiers into the drift gas.

14. The method of claim 10, wherein the drift tube is a segmented drift tube.

15. The method of claim 14, wherein the group of ions are pre-separated by a section of the segmented drift tube prior to the AC ion gate.

16. The method of claim 14, wherein the segmented drift tube is divided by multiple AC gates between pairs of adjacent segments, with each of the AC ion gates only allowing selected ions to pass that AC ion gate.

17. The method of claim 14, wherein different segments of the drift tube contain different gas compositions, including different gases and/or chemical modifiers.

18. The method of claim 10, wherein the group of ions is a mixture of solvent(s) and sample(s).

19. The method of claim 18, wherein the AC gate is operated to eliminate solvent ions from the group of ions.

* * * * *